US010314559B2

(12) United States Patent
Razzaque et al.

(10) Patent No.: US 10,314,559 B2
(45) Date of Patent: Jun. 11, 2019

(54) MEDICAL DEVICE GUIDANCE

(71) Applicant: InnerOptic Technology, Inc., Hillsborough, NC (US)

(72) Inventors: Sharif Razzaque, Chapel Hill, NC (US); Andrei State, Chapel Hill, NC (US); Brian Heaney, Durham, NC (US)

(73) Assignee: InnerOptic Technology, Inc., Hillsborough, NC (US)

( * ) Notice: Subject to any disclaimer, the term of this patent is extended or adjusted under 35 U.S.C. 154(b) by 1037 days.

(21) Appl. No.: 14/212,933

(22) Filed: Mar. 14, 2014

(65) Prior Publication Data

US 2014/0343404 A1    Nov. 20, 2014

Related U.S. Application Data

(60) Provisional application No. 61/783,044, filed on Mar. 14, 2013.

(51) Int. Cl.
*A61B 5/06* (2006.01)
*A61B 8/08* (2006.01)
(Continued)

(52) U.S. Cl.
CPC ............ *A61B 8/0841* (2013.01); *A61B 34/25* (2016.02); *A61B 2034/2048* (2016.02); *A61B 2034/2051* (2016.02); *A61B 2034/2055* (2016.02); *A61B 2090/368* (2016.02); *A61B 2090/378* (2016.02); *A61B 2090/502* (2016.02)

(58) Field of Classification Search
CPC ................. A61B 8/0841; A61B 34/25; A61B 2034/2048; A61B 2034/2051; A61B 2034/2055; A61B 2090/368; A61B 2090/378; A61B 2090/502
See application file for complete search history.

(56) References Cited

U.S. PATENT DOCUMENTS 3,556,079 A    1/1971  Omizo
4,058,114 A   11/1977  Soldner
(Continued)

FOREIGN PATENT DOCUMENTS

AU    7656896 A    5/1997
AU    9453898 A    4/1999
(Continued)

OTHER PUBLICATIONS

U.S. Appl. No. 11/828,826, filed Jul. 26, 2007, Keller et al.
(Continued)

*Primary Examiner* — Thomas J Hong
*Assistant Examiner* — Colin T. Sakamoto
(74) *Attorney, Agent, or Firm* — Knobbe, Martens, Olson & Bear, LLP

(57) ABSTRACT

A system and method for providing image guidance for placement of one or more medical devices at a target location. The system can be used to display portions of a display object, such as a rendered medical image, at different transparency levels. The system can also be used to resolve co-located display objects, such as a co-located image guidance cue and rendered medical image. The system can further be used to adjust a point-of-view location for one or more medical display objects within a virtual 3D space.

24 Claims, 10 Drawing Sheets

(51) Int. Cl.
*A61B 34/00* (2016.01)
*A61B 5/055* (2006.01)
*A61B 6/03* (2006.01)
*A61B 90/50* (2016.01)
*A61B 34/20* (2016.01)
*A61B 90/00* (2016.01)

(56) References Cited

U.S. PATENT DOCUMENTS

| | | |
|---|---|---|
| RE30,397 E | 9/1980 | King |
| 4,249,539 A | 2/1981 | Vilkomerson et al. |
| 4,294,544 A | 10/1981 | Altschuler et al. |
| 4,390,025 A | 6/1983 | Takemura et al. |
| 4,407,294 A | 10/1983 | Vilkomerso |
| 4,431,006 A | 2/1984 | Trimmer et al. |
| 4,567,896 A | 2/1986 | Barnea et al. |
| 4,583,538 A | 4/1986 | Onik et al. |
| 4,620,546 A | 11/1986 | Aida et al. |
| 4,671,292 A | 6/1987 | Matzuk |
| 4,839,836 A | 6/1989 | Fonsalas |
| 4,862,873 A | 9/1989 | Yajima et al. |
| 4,884,219 A | 11/1989 | Waldren |
| 4,899,756 A | 2/1990 | Sonek |
| 4,911,173 A | 3/1990 | Terwillige |
| 4,945,305 A | 7/1990 | Blood |
| 5,076,279 A | 12/1991 | Arenson et al. |
| 5,078,140 A | 1/1992 | Kwoh |
| 5,078,142 A | 1/1992 | Siczek et al. |
| 5,095,910 A | 3/1992 | Powers |
| 5,109,276 A | 4/1992 | Nudelman et al. |
| 5,158,088 A | 10/1992 | Nelson et al. |
| 5,161,536 A | 11/1992 | Vikomerson et al. |
| 5,193,120 A | 3/1993 | Gamache et al. |
| 5,209,235 A | 5/1993 | Brisken et al. |
| 5,249,581 A | 10/1993 | Horbal et al. |
| 5,251,127 A | 10/1993 | Raab |
| 5,261,404 A | 11/1993 | Mick et al. |
| 5,265,610 A | 11/1993 | Darrow et al. |
| 5,271,400 A | 12/1993 | Dumoulin et al. |
| 5,307,153 A | 4/1994 | Maruyama et al. |
| 5,309,913 A | 5/1994 | Kormos et al. |
| 5,323,002 A | 6/1994 | Sampsell et al. |
| 5,371,543 A | 12/1994 | Anderson |
| 5,383,454 A | 1/1995 | Bucholz |
| 5,394,875 A | 3/1995 | Lewis et al. |
| 5,411,026 A | 5/1995 | Carol |
| 5,433,198 A | 7/1995 | Desai |
| 5,433,739 A | 7/1995 | Sluijter |
| 5,443,489 A | 8/1995 | Ben-Haim |
| 5,446,798 A | 8/1995 | Morita et al. |
| 5,447,154 A | 9/1995 | Cinquin et al. |
| 5,452,024 A | 9/1995 | Sampsell |
| 5,457,493 A | 10/1995 | Leddy et al. |
| 5,474,073 A | 12/1995 | Schwartz et al. |
| 5,476,096 A | 12/1995 | Olstad et al. |
| 5,483,961 A | 1/1996 | Kelly et al. |
| 5,488,431 A | 1/1996 | Gove et al. |
| 5,489,952 A | 2/1996 | Gove et al. |
| 5,491,510 A | 2/1996 | Gove |
| 5,494,039 A | 2/1996 | Onik et al. |
| 5,503,152 A | 4/1996 | Oakley et al. |
| 5,505,204 A | 4/1996 | Picot et al. |
| 5,515,856 A | 5/1996 | Olstad et al. |
| 5,517,990 A | 5/1996 | Kalfas et al. |
| 5,526,051 A | 6/1996 | Gove et al. |
| 5,526,812 A | 6/1996 | Dumoulin et al. |
| 5,529,070 A | 6/1996 | Augustine et al. |
| 5,531,227 A | 7/1996 | Schneider |
| 5,532,997 A | 7/1996 | Pauli |
| 5,541,723 A | 7/1996 | Tanaka |
| 5,558,091 A | 9/1996 | Acker et al. |
| 5,568,811 A | 10/1996 | Olstad |
| 5,570,135 A | 10/1996 | Gove et al. |
| 5,579,026 A | 11/1996 | Tabata |
| 5,581,271 A | 12/1996 | Kraemer |
| 5,588,948 A | 12/1996 | Takahashi et al. |
| 5,608,468 A | 3/1997 | Gove et al. |
| 5,608,849 A | 3/1997 | King, Jr. |
| 5,611,345 A | 3/1997 | Hibbeln |
| 5,611,353 A | 3/1997 | Dance et al. |
| 5,612,753 A | 3/1997 | Poradish et al. |
| 5,625,408 A | 4/1997 | Matsugu et al. |
| 5,628,327 A | 5/1997 | Unger et al. |
| 5,629,794 A | 5/1997 | Magel et al. |
| 5,630,027 A | 5/1997 | Venkateswar et al. |
| 5,647,361 A | 7/1997 | Damadian |
| 5,647,373 A | 7/1997 | Paltieli et al. |
| 5,660,185 A | 8/1997 | Shmulewitz et al. |
| 5,662,111 A | 9/1997 | Cosman |
| 5,699,444 A | 12/1997 | Palm |
| 5,701,898 A | 12/1997 | Adam et al. |
| 5,701,900 A | 12/1997 | Shehada et al. |
| 5,726,670 A | 3/1998 | Tabata et al. |
| 5,728,044 A | 3/1998 | Shan |
| 5,758,650 A | 6/1998 | Miller et al. |
| 5,766,135 A | 6/1998 | Terwilliger |
| 5,784,098 A | 7/1998 | Shoji et al. |
| 5,792,147 A | 8/1998 | Evans et al. |
| 5,793,701 A | 8/1998 | Wright et al. |
| 5,797,849 A | 8/1998 | Vesely et al. |
| 5,807,395 A | 9/1998 | Mulier et al. |
| 5,810,008 A | 9/1998 | Dekel et al. |
| 5,817,022 A | 10/1998 | Vesely |
| 5,820,554 A | 10/1998 | Davis et al. |
| 5,820,561 A | 10/1998 | Olstad et al. |
| 5,829,439 A | 11/1998 | Yokosawa et al. |
| 5,829,444 A | 11/1998 | Ferre et al. |
| 5,851,183 A | 12/1998 | Bodiolz |
| 5,870,136 A | 2/1999 | Fuchs et al. |
| 5,891,034 A | 4/1999 | Bucholz |
| 5,920,395 A | 7/1999 | Schulz |
| 5,961,527 A | 10/1999 | Whitmore, III et al. |
| 5,967,980 A | 10/1999 | Ferre et al. |
| 5,967,991 A | 10/1999 | Gardineer et al. |
| 5,991,085 A | 11/1999 | Rallison et al. |
| 6,016,439 A | 1/2000 | Acker |
| 6,019,724 A | 2/2000 | Gronningsaeter et al. |
| 6,048,312 A | 4/2000 | Ishrak et al. |
| 6,064,749 A | 5/2000 | Hirota et al. |
| 6,091,546 A | 7/2000 | Spitzer |
| 6,095,982 A | 8/2000 | Richards-Kortum et al. |
| 6,099,471 A | 8/2000 | Torp et al. |
| 6,108,130 A | 8/2000 | Raj |
| 6,122,538 A | 9/2000 | Sliwa, Jr. et al. |
| 6,122,541 A | 9/2000 | Cosman et al. |
| 6,160,666 A | 12/2000 | Rallison et al. |
| 6,167,296 A | 12/2000 | Shahidi |
| 6,181,371 B1 | 1/2001 | Maguire, Jr. |
| RE37,088 E | 3/2001 | Olstad et al. |
| 6,216,029 B1 | 4/2001 | Paltieli |
| 6,241,725 B1 | 6/2001 | Cosman |
| 6,245,017 B1 | 6/2001 | Hashimoto et al. |
| 6,246,898 B1 | 6/2001 | Vesely et al. |
| 6,248,101 B1 | 6/2001 | Witmore, III et al. |
| 6,261,234 B1 | 7/2001 | Lin |
| 6,341,016 B1 | 1/2002 | Malione |
| 6,348,058 B1 | 2/2002 | Melken et al. |
| 6,350,238 B1 | 2/2002 | Olstad et al. |
| 6,352,507 B1 | 3/2002 | Torp et al. |
| 6,379,302 B1 | 4/2002 | Kessman et al. |
| 6,385,475 B1 | 5/2002 | Cinquin et al. |
| 6,442,417 B1 | 8/2002 | Shahidi et al. |
| 6,447,450 B1 | 9/2002 | Olstad |
| 6,456,868 B2 | 9/2002 | Saito et al. |
| 6,470,207 B1 | 10/2002 | Simon et al. |
| 6,471,366 B1 | 10/2002 | Hughson et al. |
| 6,477,400 B1 | 11/2002 | Barrick |
| 6,478,793 B1 | 11/2002 | Cosman et al. |
| 6,503,195 B1 | 1/2003 | Keller et al. |
| 6,511,418 B2 | 1/2003 | Shahidi et al. |
| 6,517,485 B2 | 2/2003 | Torp et al. |
| 6,518,939 B1 | 2/2003 | Kikuchi |
| 6,527,443 B1 | 3/2003 | Vilsmeier |
| 6,529,758 B2 | 3/2003 | Shahidi |

(56) References Cited

U.S. PATENT DOCUMENTS

| | | | |
|---|---|---|---|
| 6,537,217 B1 | 3/2003 | Bjaerum et al. |
| 6,545,706 B1 | 4/2003 | Edwards et al. |
| 6,546,279 B1 | 4/2003 | Bova et al. |
| 6,551,325 B2 | 4/2003 | Neubauer et al. |
| 6,570,566 B1 | 5/2003 | Yoshigahara |
| 6,575,969 B1 | 6/2003 | Rittman, III et al. |
| 6,579,240 B2 | 6/2003 | Bjaerum et al. |
| 6,587,711 B1 | 7/2003 | Alfano et al. |
| 6,591,130 B2 | 7/2003 | Shahidi |
| 6,592,522 B2 | 7/2003 | Bjaerum et al. |
| 6,594,517 B1 | 7/2003 | Nevo |
| 6,597,818 B2 | 7/2003 | Kumar et al. |
| 6,604,404 B2 | 8/2003 | Paltieli et al. |
| 6,616,610 B2 | 9/2003 | Steininger et al. |
| 6,626,832 B1 | 9/2003 | Paltieli et al. |
| 6,652,462 B2 | 11/2003 | Bjaerum et al. |
| 6,669,635 B2 | 12/2003 | Kessman et al. |
| 6,676,599 B2 | 1/2004 | Torp et al. |
| 6,689,067 B2 | 2/2004 | Sauer et al. |
| 6,695,786 B2 | 2/2004 | Wang et al. |
| 6,711,429 B1 | 3/2004 | Gilboa et al. |
| 6,725,082 B2 | 4/2004 | Sati et al. |
| 6,733,458 B1 | 5/2004 | Steins et al. |
| 6,764,449 B2 | 7/2004 | Lee et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,863,655 B2 | 3/2005 | Bjaerum et al. |
| 6,873,867 B2 | 3/2005 | Vilsmeier |
| 6,875,179 B2 | 4/2005 | Ferguson et al. |
| 6,881,214 B2 | 4/2005 | Cosman et al. |
| 6,895,268 B1 | 5/2005 | Rahn et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,936,048 B2 | 8/2005 | Hurst |
| 6,947,783 B2 | 9/2005 | Immerz |
| 6,968,224 B2 | 11/2005 | Kessman et al. |
| 6,978,167 B2 | 12/2005 | Dekel et al. |
| 7,008,373 B2 | 3/2006 | Stoianovici et al. |
| 7,033,360 B2 | 4/2006 | Cinquin et al. |
| 7,072,707 B2 | 7/2006 | Galloway, Jr. et al. |
| 7,077,807 B2 | 7/2006 | Torp et al. |
| 7,093,012 B2 | 8/2006 | Olstad et al. |
| 7,110,013 B2 | 9/2006 | Ebersole et al. |
| 7,171,255 B2 | 1/2007 | Holupka et al. |
| 7,209,776 B2 | 4/2007 | Leitner |
| 7,245,746 B2 | 7/2007 | Bjaerum et al. |
| 7,248,232 B1 | 7/2007 | Yamazaki et al. |
| 7,261,694 B2 | 8/2007 | Torp et al. |
| 7,313,430 B2 | 12/2007 | Urquhart et al. |
| 7,331,932 B2 | 2/2008 | Leitner |
| 7,351,205 B2 | 4/2008 | Szczech et al. |
| 7,379,769 B2 | 5/2008 | Piron et al. |
| 7,385,708 B2 | 6/2008 | Ackerman et al. |
| 7,392,076 B2 | 6/2008 | Moctezuma de la Barrera |
| 7,398,116 B2 | 7/2008 | Edwards |
| 7,466,303 B2 | 12/2008 | Yi et al. |
| 7,480,533 B2 | 1/2009 | Cosman et al. |
| 7,505,809 B2 | 3/2009 | Strommer et al. |
| 7,588,541 B2 | 9/2009 | Floyd et al. |
| 7,596,267 B2 | 9/2009 | Accomazzi et al. |
| 7,652,259 B2 | 1/2010 | Kimchy et al. |
| 7,662,128 B2 | 2/2010 | Salcudean et al. |
| 7,678,052 B2 | 3/2010 | Torp et al. |
| 7,728,868 B2 | 6/2010 | Razzaque et al. |
| 7,747,305 B2 | 6/2010 | Dean et al. |
| 7,797,032 B2 | 9/2010 | Martinelli et al. |
| 7,798,965 B2 | 9/2010 | Torp et al. |
| 7,833,168 B2 | 11/2010 | Taylor et al. |
| 7,833,221 B2 | 11/2010 | Voegele et al. |
| 7,846,103 B2 | 12/2010 | Cannon, Jr. et al. |
| 7,876,942 B2 | 1/2011 | Gilboa |
| 7,889,905 B2 | 2/2011 | Higgins et al. |
| 7,901,357 B2 | 3/2011 | Boctor et al. |
| 7,912,849 B2 | 3/2011 | Ohrn et al. |
| 7,920,909 B2 | 4/2011 | Lyon et al. |
| 7,962,193 B2 | 6/2011 | Edwards et al. |
| 7,976,469 B2 | 7/2011 | Bonde et al. |
| 8,023,712 B2 * | 9/2011 | Ikuma ............... A61B 5/06 382/128 |
| 8,038,631 B1 | 10/2011 | Sanghvi et al. |
| 8,041,413 B2 | 10/2011 | Barbagli et al. |
| 8,050,736 B2 | 11/2011 | Piron et al. |
| 8,052,636 B2 | 11/2011 | Moll et al. |
| 8,066,644 B2 | 11/2011 | Sarkar et al. |
| 8,073,528 B2 | 12/2011 | Zhao et al. |
| 8,086,298 B2 | 12/2011 | Whitmore, III et al. |
| 8,135,669 B2 | 3/2012 | Olstad et al. |
| 8,137,281 B2 | 3/2012 | Huang et al. |
| 8,147,408 B2 | 4/2012 | Bunce et al. |
| 8,152,724 B2 | 4/2012 | Ridley et al. |
| 8,167,805 B2 | 5/2012 | Emery et al. |
| 8,216,149 B2 | 7/2012 | Oonuki et al. |
| 8,221,322 B2 | 7/2012 | Wang et al. |
| 8,228,028 B2 | 7/2012 | Schneider |
| 8,257,264 B2 | 9/2012 | Park et al. |
| 8,296,797 B2 | 10/2012 | Olstad et al. |
| 8,340,379 B2 | 12/2012 | Razzaque et al. |
| 8,350,902 B2 | 1/2013 | Razzaque et al. |
| 8,482,606 B2 | 7/2013 | Razzaque et al. |
| 8,554,307 B2 | 10/2013 | Razzaque et al. |
| 8,585,598 B2 | 11/2013 | Razzaque et al. |
| 8,641,621 B2 | 2/2014 | Razzaque et al. |
| 8,670,816 B2 | 3/2014 | Green et al. |
| 8,690,776 B2 | 4/2014 | Razzaque et al. |
| 8,831,310 B2 | 9/2014 | Razzaque et al. |
| 9,364,294 B2 | 6/2016 | Razzaque et al. |
| 9,398,936 B2 | 7/2016 | Razzaque et al. |
| 9,901,406 B2 | 2/2018 | State et al. |
| 9,949,700 B2 | 4/2018 | Razzaque et al. |
| 2001/0007919 A1 | 7/2001 | Shahidi |
| 2001/0016804 A1 | 8/2001 | Cunningham et al. |
| 2001/0041838 A1 | 11/2001 | Holupka et al. |
| 2001/0045979 A1 | 11/2001 | Matsumoto et al. |
| 2002/0010384 A1 | 1/2002 | Shahidi et al. |
| 2002/0032772 A1 | 3/2002 | Olstad et al. |
| 2002/0049375 A1 | 4/2002 | Strommer et al. |
| 2002/0077540 A1 | 6/2002 | Kienzle, III |
| 2002/0077543 A1 | 6/2002 | Grzeszczuk et al. |
| 2002/0103431 A1 | 8/2002 | Toker et al. |
| 2002/0105484 A1 | 8/2002 | Navab et al. |
| 2002/0135673 A1 | 9/2002 | Favalora et al. |
| 2002/0138008 A1 | 9/2002 | Tsujita et al. |
| 2002/0140814 A1 | 10/2002 | Cohen-Solal et al. |
| 2002/0156375 A1 | 10/2002 | Kessmam et al. |
| 2002/0198451 A1 | 12/2002 | Carson |
| 2003/0040743 A1 | 2/2003 | Cosman et al. |
| 2003/0073901 A1 | 4/2003 | Simon et al. |
| 2003/0135119 A1 | 7/2003 | Lee et al. |
| 2003/0163142 A1 | 8/2003 | Paltieli et al. |
| 2003/0164172 A1 | 9/2003 | Chumas et al. |
| 2003/0231789 A1 | 12/2003 | Willis et al. |
| 2004/0034313 A1 | 2/2004 | Leitner |
| 2004/0078036 A1 | 4/2004 | Keidar |
| 2004/0095507 A1 | 5/2004 | Bishop et al. |
| 2004/0116810 A1 | 6/2004 | Olstad |
| 2004/0147920 A1 | 7/2004 | Keidar |
| 2004/0152970 A1 | 8/2004 | Hunter et al. |
| 2004/0181144 A1 | 9/2004 | Cinquin et al. |
| 2004/0215071 A1 | 10/2004 | Frank et al. |
| 2004/0238732 A1 | 12/2004 | State et al. |
| 2004/0243146 A1 | 12/2004 | Chesbrough et al. |
| 2004/0243148 A1 | 12/2004 | Wasielewski |
| 2004/0249281 A1 | 12/2004 | Olstad |
| 2004/0249282 A1 | 12/2004 | Olstad |
| 2004/0254454 A1 | 12/2004 | Kockro |
| 2005/0010098 A1 | 1/2005 | Frigstad et al. |
| 2005/0085717 A1 | 4/2005 | Shahidi |
| 2005/0085718 A1 | 4/2005 | Shahidi |
| 2005/0090742 A1 | 4/2005 | Mine et al. |

(56) References Cited

U.S. PATENT DOCUMENTS

| | | |
|---|---|---|
| 2005/0107679 A1 | 5/2005 | Geiger et al. |
| 2005/0111733 A1 | 5/2005 | Fors et al. |
| 2005/0159641 A1 | 7/2005 | Kanai |
| 2005/0182316 A1 | 8/2005 | Burdette et al. |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0231532 A1* | 10/2005 | Suzuki .................... G06F 3/012 345/633 |
| 2005/0251148 A1 | 11/2005 | Friedrich |
| 2006/0020204 A1 | 1/2006 | Serra et al. |
| 2006/0036162 A1 | 2/2006 | Shahidi et al. |
| 2006/0052792 A1 | 3/2006 | Boettiger et al. |
| 2006/0058609 A1 | 3/2006 | Olstad |
| 2006/0058610 A1 | 3/2006 | Olstad |
| 2006/0058674 A1 | 3/2006 | Olstad |
| 2006/0058675 A1 | 3/2006 | Olstad |
| 2006/0100505 A1 | 5/2006 | Viswanathan |
| 2006/0004275 A1 | 6/2006 | Vija et al. |
| 2006/0122495 A1 | 6/2006 | Cosman et al. |
| 2006/0184040 A1 | 8/2006 | Keller et al. |
| 2006/0193504 A1 | 8/2006 | Salgo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0241450 A1 | 10/2006 | Da Silva et al. |
| 2006/0253030 A1 | 11/2006 | Altmann et al. |
| 2006/0253032 A1 | 11/2006 | Altmann et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0002582 A1 | 1/2007 | Burwell et al. |
| 2007/0016035 A1 | 1/2007 | Hashimoto |
| 2007/0032906 A1 | 2/2007 | Sutherland et al. |
| 2007/0073155 A1 | 3/2007 | Park et al. |
| 2007/0073455 A1 | 3/2007 | Park et al. |
| 2007/0078346 A1 | 4/2007 | Park et al. |
| 2007/0167699 A1 | 7/2007 | Lathuiliere et al. |
| 2007/0167701 A1 | 7/2007 | Sherman |
| 2007/0167705 A1 | 7/2007 | Chiang et al. |
| 2007/0167771 A1 | 7/2007 | Olstad |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0255136 A1 | 11/2007 | Kjell et al. |
| 2007/0270718 A1 | 11/2007 | Rochetin et al. |
| 2007/0276234 A1 | 11/2007 | Shahidi |
| 2007/0291000 A1 | 12/2007 | Liang et al. |
| 2008/0004481 A1 | 1/2008 | Bax et al. |
| 2008/0004516 A1 | 1/2008 | DiSilvestro et al. |
| 2008/0030578 A1 | 2/2008 | Razzaque et al. |
| 2008/0039723 A1 | 2/2008 | Suri et al. |
| 2008/0051910 A1 | 2/2008 | Kammerzell et al. |
| 2008/0091106 A1 | 4/2008 | Kim et al. |
| 2008/0114235 A1 | 5/2008 | Unal et al. |
| 2008/0146939 A1 | 6/2008 | McMorrow et al. |
| 2008/0161824 A1 | 7/2008 | McMillen |
| 2008/0183080 A1 | 7/2008 | Abraham |
| 2008/0200794 A1 | 8/2008 | Teichman et al. |
| 2008/0208031 A1 | 8/2008 | Kurpad et al. |
| 2008/0208081 A1 | 8/2008 | Murphy et al. |
| 2008/0214932 A1 | 9/2008 | Mollard et al. |
| 2008/0232679 A1 | 9/2008 | Hahn et al. |
| 2008/0287794 A1 | 11/2008 | Li et al. |
| 2008/0287805 A1 | 11/2008 | Li |
| 2008/0287837 A1 | 11/2008 | Makin et al. |
| 2009/0024030 A1 | 1/2009 | Lachaine et al. |
| 2009/0036902 A1 | 2/2009 | DiMaio et al. |
| 2009/0105597 A1 | 4/2009 | Abraham |
| 2009/0118613 A1 | 5/2009 | Krugman et al. |
| 2009/0118724 A1 | 5/2009 | Zvuloni et al. |
| 2009/0131783 A1 | 5/2009 | Jenkins et al. |
| 2009/0137907 A1 | 5/2009 | Takimoto et al. |
| 2009/0175518 A1* | 7/2009 | Ikuma .................... A61B 5/06 382/128 |
| 2009/0226069 A1 | 9/2009 | Razzaque et al. |
| 2009/0234369 A1 | 9/2009 | Bax et al. |
| 2009/0312629 A1 | 12/2009 | Razzaque et al. |
| 2010/0045783 A1 | 2/2010 | State et al. |
| 2010/0152570 A1 | 6/2010 | Navab |
| 2010/0185087 A1 | 7/2010 | Nields et al. |
| 2010/0198045 A1 | 8/2010 | Razzaque et al. |
| 2010/0208963 A1 | 8/2010 | Kruecker et al. |
| 2010/0268067 A1* | 10/2010 | Razzaque .......... A61B 18/1477 600/424 |
| 2010/0268072 A1 | 10/2010 | Hall et al. |
| 2010/0268085 A1 | 10/2010 | Kruecker et al. |
| 2010/0296718 A1 | 11/2010 | Ostrovsky-Berman et al. |
| 2010/0298705 A1 | 11/2010 | Pelissier et al. |
| 2010/0305448 A1 | 12/2010 | Dagonnau et al. |
| 2010/0312121 A1 | 12/2010 | Guan |
| 2010/0331252 A1 | 12/2010 | Clements et al. |
| 2011/0043612 A1 | 2/2011 | Keller et al. |
| 2011/0046483 A1 | 2/2011 | Fuchs et al. |
| 2011/0046486 A1 | 2/2011 | Shin et al. |
| 2011/0057930 A1 | 3/2011 | Keller |
| 2011/0082351 A1 | 4/2011 | Razzaque et al. |
| 2011/0130641 A1 | 6/2011 | Razzaque et al. |
| 2011/0137156 A1 | 6/2011 | Razzaque et al. |
| 2011/0201915 A1 | 8/2011 | Gogin et al. |
| 2011/0201976 A1 | 8/2011 | Sanghvi et al. |
| 2011/0230351 A1 | 9/2011 | Fischer et al. |
| 2011/0237947 A1 | 9/2011 | Boctor et al. |
| 2011/0238043 A1 | 9/2011 | Kleven |
| 2011/0251483 A1 | 10/2011 | Razzaque et al. |
| 2011/0274324 A1 | 11/2011 | Clements et al. |
| 2011/0282188 A1 | 11/2011 | Burnside et al. |
| 2011/0288412 A1 | 11/2011 | Deckman et al. |
| 2011/0295108 A1 | 12/2011 | Cox et al. |
| 2011/0301451 A1 | 12/2011 | Rohling |
| 2012/0035473 A1 | 2/2012 | Sanghvi et al. |
| 2012/0059260 A1 | 3/2012 | Robinson |
| 2012/0071759 A1 | 3/2012 | Hagy et al. |
| 2012/0078094 A1 | 3/2012 | Nishina et al. |
| 2012/0101370 A1 | 4/2012 | Razzaque et al. |
| 2012/0108955 A1 | 5/2012 | Razzaque et al. |
| 2012/0138658 A1 | 6/2012 | Ullrich et al. |
| 2012/0143029 A1 | 6/2012 | Silverstein et al. |
| 2012/0143055 A1 | 6/2012 | Cheng et al. |
| 2012/0165679 A1 | 6/2012 | Orome et al. |
| 2012/0237105 A1 | 9/2012 | Mielekamp |
| 2012/0259210 A1 | 10/2012 | Harhen et al. |
| 2013/0030286 A1 | 1/2013 | Alouani et al. |
| 2013/0044930 A1 | 2/2013 | Li et al. |
| 2013/0079770 A1 | 3/2013 | Kyle, Jr. et al. |
| 2013/0096497 A1 | 4/2013 | Duindam et al. |
| 2013/0132374 A1 | 5/2013 | Olstad et al. |
| 2013/0151533 A1 | 6/2013 | Udupa et al. |
| 2013/0178745 A1 | 7/2013 | Kyle et al. |
| 2013/0218024 A1 | 8/2013 | Boctor et al. |
| 2013/0249787 A1 | 9/2013 | Morimoto |
| 2014/0016848 A1 | 1/2014 | Razzaque et al. |
| 2014/0051987 A1 | 2/2014 | Kowshik et al. |
| 2014/0078138 A1 | 3/2014 | Martin et al. |
| 2014/0094687 A1 | 4/2014 | Razzaque |
| 2014/0180074 A1 | 6/2014 | Green |
| 2014/0201669 A1 | 7/2014 | Liu et al. |
| 2014/0275760 A1 | 9/2014 | Lee et al. |
| 2014/0275810 A1 | 9/2014 | Keller et al. |
| 2014/0275997 A1 | 9/2014 | Chopra et al. |
| 2014/0350390 A1 | 11/2014 | Kudavelly et al. |
| 2016/0117857 A1 | 4/2016 | State et al. |
| 2016/0166334 A1 | 6/2016 | Razzaque |
| 2016/0166336 A1 | 6/2016 | Razzaque |
| 2016/0196694 A1 | 7/2016 | Lindeman |
| 2017/0024903 A1 | 1/2017 | Razzaque |
| 2017/0323424 A1 | 11/2017 | Razzaque et al. |
| 2017/0348067 A1 | 12/2017 | Krimsky |
| 2017/0360395 A1 | 12/2017 | Razzaque et al. |
| 2018/0116731 A1 | 5/2018 | State et al. |

(56) References Cited

U.S. PATENT DOCUMENTS

FOREIGN PATENT DOCUMENTS

| | | |
|---|---|---|
| AU | 1719601 A | 6/2001 |
| AU | 9036301 A | 3/2002 |
| AU | 2003297225 A1 | 7/2004 |
| AU | 2001290363 B2 | 2/2006 |
| BR | 0113882 A | 7/2003 |
| CA | 2420382 C | 4/2011 |
| DE | 60126798 T2 | 10/2007 |
| EP | 0 427 358 | 5/1991 |
| EP | 1955284 | 8/2008 |
| JP | S63-290550 A | 11/1988 |
| JP | H07-116164 A | 5/1995 |
| JP | 2005-058584 | 3/2005 |
| JP | 2005-323669 | 11/2005 |
| JP | 2009-517177 | 4/2009 |
| WO | WO 96/005768 | 2/1996 |
| WO | WO 97/015249 | 5/1997 |
| WO | WO 97/017014 | 5/1997 |
| WO | WO 97/029682 | 8/1997 |
| WO | WO 99/26534 | 6/1999 |
| WO | WO 01/039683 | 6/2001 |
| WO | WO 03/032837 | 4/2003 |
| WO | WO 03/034705 | 4/2003 |
| WO | PCT/US2003/17987 | 12/2003 |
| WO | WO 03/105289 | 12/2003 |
| WO | WO 05/010711 | 2/2005 |
| WO | WO 07/019216 | 2/2007 |
| WO | WO 07/067323 A2 | 6/2007 |
| WO | WO 07/067323 A3 | 9/2007 |
| WO | WO 08/017051 | 2/2008 |
| WO | WO 09/094646 | 7/2009 |
| WO | WO 10/057315 | 5/2010 |
| WO | WO 10/096419 | 8/2010 |
| WO | WO 09/063423 | 10/2010 |
| WO | WO 11/014687 | 2/2011 |
| WO | WO 12/169990 A2 | 12/2012 |
| WO | WO 13/116240 | 8/2013 |
| WO | WO 18/080844 | 5/2018 |

OTHER PUBLICATIONS

"3D Laparoscope Technology," http://www.inneroptic.com/tech_3DL.htm, copyright 2007 InnerOptic Technology, Inc. printed Sep. 19, 2007, 2 pages.
"Cancer Facts & Figures 2004," www.cancer.org/downloads/STT/CAFF_finalPWSecured.pdf, copyright 2004 American Cancer Society, Inc., printed Sep. 19, 2007, 60 pages.
"David Laserscanner <—Latest News <—Institute for Robotics and Process Control <—Te . . . ," http://www/rob.cs.tu-bs.de/en/news/david, printed Sep. 19, 2007, 1 page.
"Laser scanned 3d model Final" video, still image of video attached, http://www.youtube.com/watch?v+DaLglgmoUf8, copyright 2007 YouTube, LLC, printed Sep. 19, 2007, 2 pages.
"Olympus Endoscopic Ultrasound System," www.olympusamerica.com/msg_section/download_brochures/135_b_gfum130.pdf, printed Sep. 20, 2007, 20 pages.
"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.
"Robbins, Mike—Computer Vision Research—Stereo Depth Perception," http://www.compumike.com/vision/stereodepth. php, copyright 2007 Michael F. Robbins, printed Sep. 19, 2007, 3 pages.
"Rue, Registered Ultrasound-Endoscope," copyright 2007 InnerOptic Technology, Inc., 2 pages.
Advertisement, "Inspeck 3DC 3D Capturor," Inspeck 3DC 3D Capturor (www.inspeck.com), 1998.
Advertisement, "Virtual 3D High Speed Non-Contact Surface Perception," Virtual 3-D Technologies Corporation (www.virtual3dtech.com)., Dec. 21, 1998.
Advertisements, "Virtuoso," Visual Interface, Inc. (www.visint.com), Dec. 21, 1998.
Akka, "Automatic Software Control of Display Parameters for Stereoscopic Graphics Images," SPIE vol. 1669: Stereoscopic Displays and Applications III, pp. 31-38 (1992).
Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.
Aylward et al., Analysis of the Parameter Space of a Metric for Registering 3D Vascular Images, in W. Niessen and M. Viergever (Eds.): MICCAI 2001, LNCS 2208, pp. 932-939, 2001.
Aylward et al., Registration and Analysis of Vascular Images, International Journal of Computer Vision 55(2/3), 123-138, 2003.
Aylward, et al., Intra-Operative 3D Ultrasound Augmentation, Proceedings of the IEEE International Symposium on Biomedical Imaging, Washington, Jul. 2002.
Azuma, "A Survey of Augmented Reality," Presence: Teleoperators and Virtual Environments 6, 4:1-48 (Aug. 1997).
Bajura, Michael et al.,, "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/MergVirtObjs92.pdf, printed Sep. 20, 2007, 8 pages.
Benavides et al., "Multispectral digital colposcopy for in vivo detection of cervical cancer," Optics Express; May 19, 2003; 11(10) Optical Society of America; USA.
Beraldin, J.A. et al., "Optimized Position Sensors for Flying-Spot Active Triangulation Systems," Proceedings of the Fourth International Conference on a 3-D Digital Imaging and Modeling (3DIM), Banff, Alberta, Canada, Oct. 6-10, 2003, pp. 334-341, NRC 47083, copyright 2003 National Research Council of Canada, http://iit-iti.nrc-cnrc.gc.ca/iit-publications-iti/docs/NRC-47083.pdf, printed Sep. 19, 2007, 9 pages.
Billinghurst, M. et al., Research Directions in Handheld AR; Int. J. of Virtual Reality 5(2),51-58 (2006).
Bishop, Azuma et al., "Improving Static and Dynamic Registration in an Optical See-Through HMD," Paper Presented at SIGGRAPH '94 Annual Conference in Orlando, FL (1994).
Blais, F., "Review of 20 Years of Range Sensor Development," Journal of Electronic Imaging, 13(1): 231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.
Bouguet, Jean-Yves, "Camera Calibration Toolbox for Matlab," www.vision.caltech.edu/bouguetj/calib_doc, printed Sep. 20, 2007, 5 pages.
Buxton et al.; "Colposcopically directed punch biopsy: a potentially misleading investigation," British Journal of Obstetrics and Gynecology; Dec. 1991; 98:1273-1276.
Caines, Judy S. et al. Stereotaxic Needle Core Biopsy of Breast Lesions Using a Regular Mammographic Table with an Adaptable Stereotaxic Device, American Journal of Roentgenology, vol. 163, No. 2, Aug. 1994, pp. 317-321. Downloaded from www.ajrorline.org on Jul. 10, 2013.
Cancer Prevention & Early Detection Facts & Figures 2004; National Center for Tobacco-Free Kids; 2004; American Cancer Society; USA.
Cantor et al., "Cost-Effectiveness Analysis of Diagnosis and Management of Cervical Squamous Intraepithelial Lesions," Diagnostic Strategies for SILs; Feb. 1998; 91(2):270-277.
Catalano et al. "Multiphase helical CT findings after percutaneous ablation procedures for hepatocellular carcinoma." Abdom. Imaging, 25(6),2000, pp. 607-614.
Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1): 219-229.
Crawford, David E. et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.

(56) References Cited

OTHER PUBLICATIONS

Deering, Michael "High Resolution Virtual Reality." Proceedings of SIGGRAPH '92, Computer Graphics, 26(2), 1992, pp. 195-202.
Depiero et al., "3-D Computer Vision Using Structured Light: Design, Calibration and Implementation Issues," The University of Tennessee, pp. 1-46, (1996).
Dodd, G.D. et al. "Minimally invasive treatment of malignant hepatic tumors: at the threshold of a major breakthrough." Radiographies 20(1),2000, pp. 9-27.
Drascic et al., "Perceptual Issues in Augmented Reality," SPIE vol. 2653: Stereoscopic Displays and Virtual Reality Systems III, pp. 123-134 (Feb. 1996).
Dumoulin, C.L. et al, Real-Time Position Monitoring of Invasive Devices Using Magnetic Resonance, Magnetic Resonance in Medicine, vol. 29, Issue 3, Mar. 1993, pp. 411-415.
Fahey et al., "Meta-analysis of Pap Test Accuracy; American Journal of Epidemiology," 1995 141(7):680-689; The John Hopkins University School of Hyqiene and Public Health; USA.
Foxlin et al., "An Inertial Head-Orientation Tracker with Automatic Drift Compensation for Use with HMD's," Proceedings of the 1994 Virtual Reality Software and Technology Conference, Aug. 23-26, 1994, Singapore, pp. 159-173 (1994).
Fronheiser et al., Real-Time 3D Color Doppler for Guidance of Vibrating Interventional Devices, IEEE Ultrasonics Symposium, pp. 149-152 (2004).
Fuchs, Henry et al. "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications/AugRealVis_LaparoSurg98.pdf, printed Sep. 20, 2007, 10 pages.
Fuchs, et al.: "Optimizing a Head-Tracked Stereo Display System to Guide Hepatic Tumor Ablation," Departments of Computer Sciences and Radiology, and School of Medicine, University of North Carolina at Chapel Hill; InnerOptic Technology, Inc. 2008.
Fuchs, et al.: "Virtual Environments Technology to Aid Needle Biopsies of the Breast," Health Care in the Information Age, Ch. 6, pp. 60-61, Presented in San Diego, Jan. 17-20, 1996, published by IOS Press and Ohmsha Feb. 1996.
Garrett, William F. et al., "Real-Time Incremental Visualization of Dynamic Ultrasound Volumes Using Parallel BSP Trees," Proceedings of IEEE Visualization 1996, pp. 235-240, available from www.cs.unc.edu/~andrei/pubs/1996_VIS_dualBSP_Mac.pdf, printed Sep. 20, 2007, 7 pages.
Georgakoudi et al., "Trimodal spectroscopy for the detection and characterization of cervical precancers in vivo," American Journal of Obstetrics and Gynecology; Mar. 2002; 186(3):374-382; USA.
Herline et al., Surface Registration for Use in Interactive, Image-Guided Liver Surgery, Computer Aided Surgery 5:11-17 (2000).
Holloway, R.; Registration Error Analysis for Augmented Reality; Presence: Teleoperators and Virtual Environments 6(4), 413-432 (1997).
Hornung et al., "Quantitative near-infrared spectroscopy of cervical dysplasia in vivo," Human Reproduction; 1999; 14(11):2908-2916; European Society of Human Reproduction and Embryology.
Howard, M.D., et al.: "An Electronic Device for Needle Placement during Sonographically Guided Percutaneous Intervention", Radiology 2001; 218:905-911.
InnerAim Brochure; 3D Visualization Software for Simpler, Safer, more Precise Aiming, Published no earlier than Apr. 1, 2010.
InVision System Brochure; A "GPS" for Real-Time 3D Needle Visualization & Guidance, Published no earlier than Mar. 1, 2008.
InVision User Manual; Professional Instructions for Use, Published no earlier than Dec. 1, 2008.
Jacobs, Marco C. et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.

Jolesz, Ferenc A, M.D., et al. MRI-Guided Laser-Induced Interstitial Thermotherapy: Basic Principles, SPIE Institute on Laser-Induced Interstitial Thermotherapy (L1TT), Jun. 22-23, 1995, Berlin, Germany.
Kadi, A Majeed, et al., Design and Simulation of an Articulated Surgical Arm for Guidling Sterotactic Neurosurgery, SPIE vol. 1708 Applications of Artificial Intelligence X: Machine Vision and Robotics (1992). Downloaded from: http://proceedings.spiedigitallibrary.org/ on Jul. 11, 2013.
Kanbara et al., "A Stereoscopic Video See-through Augmented Reality System Based on Real-time Vision-Based Registration," Nara Institute of Science and Technology, pp. 1-8 (2000).
Kato, Amami, et al., A frameless, armless navigational system for computer-assisted neurosurgery, Journal of Neurosurgery, vol. 74, No. 5, May 1991, pp. 845-849.
Lass, Amir, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.
Lee et al., "Modeling Real Objects Using Video See-Through Augmented Reality," Presence, 11(2):144-157 (Apr. 2002).
Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.
Levy, et al., An Internet-Connected, Patient Specific, Deformable Brain Atlas Integrated into a Surgical Navigation System, Journal of Digital Imaging, vol. 10, No. 3. Suppl. 1 Aug. 1997: pp. 231-237.
Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.
Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).
Meehan, Michael et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 9 pages.
Milgram et al., "Adaptation Effects in Stereo due to Online Changes in Camera Configuration," SPIE vol. 1669-13, Stereoscopic Displays and Applications III, pp. 1-12 (1992).
Mtchell et al., "Colposcopy for the Diagnosis of Squamous Intraepithelial lesions: A metaanalysis," Obstetrics and Gynecology; Apr. 1998; 91(4):626-631.
Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.
Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.
Ohbuchi et al. "An Incremental Volume Rendering Algorithm for Interactive 3D Ultrasound Imaging", UNC-CH Computer Science Technical Report TR91-003, (1991).
Ohbuchi et al., "Incremental Volume Reconstruction and Rendering for 3D Ultrasound Imaging," Visualization in Biomedical Computing, SPIE Proceedings, pp. 312-323, (Oct. 13, 1992).
Ohbuchi, "Incremental Acquisition and Visualization of 3D Ultrasound Images," Ph.D. Dissertation, UNC-CH Computer Science Technical Report TR95-023, (1993).
PCT, International Search Report and Written Opinion, re PCT Application No. PCT/US07/75122, dated Aug. 20, 2008.
PCT, International Preliminary Report on Patentability, re PCT Application No. PCT/US07/75122, dated Mar. 3, 2009.
PCT, International Search Report and Written Opinion, re PCT Application No. PCT/US2010/024378, dated Oct. 13, 2010.
PCT, International Search Report and Written Opinion, re PCT Application No. PCT/US2010/043760, dated Mar. 3, 2011.

(56) References Cited

OTHER PUBLICATIONS

PCT, The International Search Report and Written Opinion of the International Searching Authority, dated Sep. 9, 2009, for case PCT/US2009/032028.
PCT International Search Report and Written Opinion, re PCT Application No. PCT/US2013/023678, dated Jun. 13, 2013.
Progue, Brian W. et al., "Analysis of acetic acid-induced whitening of high-grade squamous intraepitheliallesions," Journal of Biomedical Optics; Oct. 2001; 6(4):397-403.
Raij, A.B., et al., Comparing Interpersonal Interactions with a Virtual Human to Those with a Real Human; IEEE Transactions on Visualization and Computer Graphics 13(3), 443-457 (2007).
Raz et al, Real-Time Magnetic Resonance Imaging—Guided Focal Laser Therapy in Patients with Low-Risk Prostate Cancer, European Urology 58, pp. 173-177. Mar. 12, 2010.
Robinett et al., "A Computational Model for the Stereoscopic Optics of a Head-Mounted Display," SPIE vol. 1457, Stereoscopic Displays and Applications II, pp. 140-160 (1991).
Rolland et al., Towards Quantifying Depth and Size Perception in Virtual Environments, Presence: Teleoperators and Virtual Environments, Winter 1995, vol. 4, Issue 1, pp. 1-21 and 24-49.
Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.
Rosenthal, Michael et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.
Screenshots from video produced by the University of North Carolina, produced circa 1992, Screenshots from video produced by the University of North Carolina, produced circa 1992.
Splechtna, Fuhrmann A. et al., Comprehensive calibration and registration procedures for augmented reality; Proc. Eurographics Workshop on Virtual Environments 2001,219-228 (2001).
State et al., "Case Study: Observing a Volume Rendered Fetus within a Pregnant Patient," Proceedings of IEEE Visualization 1994, pp. 364-368, available from www.cs.unc.edu/~fuchs/publicationsics-ObservVolRendFetus94.pdf, printed Sep. 20, 2007, 5 pages.
State et al., "Interactive Volume Visualization on a Heterogenous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007.
State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.
State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).
State et al., "Superior Augmented Reality Registration by Integrating Landmark Tracking and Magnetic Tracking," ACM SIGGRAPH Computer Graphics, Proceedings of SIGGRAPH 1996, pp. 429-438, available from www.cs.princeton.edu/courses/archive/fall01/cs597d/papers/state96.pdf, printed Sep. 20, 20007, 10 pages.
State et al., "Technologies for Augmented Reality Systems: Realizing Ultrasound-Guided Needle Biopsies," Computer Graphics, Proceedings of SIGGRAPH 1996, pp. 429-438, available from www.cs.princeton.edu/courses/archive/fall01/cs597d/papers/state96.pdf, printed Sep. 20, 2007.
State, Andrei "Exact Eye Contact with Virtual Humans." Proc. IEEE International Workshop on Human Computer Interaction 2007 (Rio de Janeiro, Brazil, Oct. 20, 2007), pp. 138-145.
State, et al.: Contextually Enhanced 3D Visualization for Multi-Born Tumor Ablation Guidance, Departments of Computer Science and Radiology, and School of Medicine, University of North Carolina at Chapel Hill; InnerOptic Technology, Inc. 2008, Chapel Hill, NC, pp. 70-77.
Takagi et al., "Development of a Stereo Video See-through HMD for AR Systems," IEEE, pp. 68-77 (2000).
Ultraguide 1000 System, Ultraguide, www.ultraguideinc.com, 1998.
Van Staveren et al., "Light Scattering in Intralipid-10% in the wavelength range of 400-1100 nm," Applied Optics; Nov. 1991; 30(31):4507-4514.
Viola et al., "Alignment by Maximization of Mutual Information," International Journal of Computer Vision, vol. 24, No. 2, pp. 1-29 (1997).
Viola, Paul A., Alignment by Maximization of Mutual Information, Ph.D. Dissertation, MIT—Artificial Intelligence Laboratory Technical Report No. 1548 (Jun. 1995).
Ware et al., "Dynamic Adjustment of Stereo Display Parameters," IEEE Transactions on Systems, Many and Cybernetics, 28(1):1-19 (1998).
Watson et al., "Using Texture Maps to Correct for Optical Distortion in Head-Mounted Displays," Proceedings of the Virtual Reality Annual Symposium '95, IEEE, pp. 1-7 (1995).
Welch, Hybrid Self-Tracker: An Inertial/Optical Hybrid Three-Dimensional Tracking System, University of North Carolina Chapel Hill Department of Computer Science, TR 95-048 (1995).
Yinghui et al., Real-Time Deformation Using Modal Analysis on Graphics Hardware, Graphite 2006, Kuala Lumpur, Malaysia, Nov. 29-Dec. 2, 2006.
Zitnick et al., "Multi-Base Stereo Using Surface Extraction," Visual Interface Inc., (Nov. 24, 1996).
Badler et al., "Simulating Humans: Computer Graphics, Animation, and Control," Oxford University Press (1993).
Fuhrmann et al. "Comprehensive calibration and registration procedures for augmented reality," Proc. Eurographics Workshop on Virtual Environments 2001, 9 pages (2001).
StereoMirror Technology Webpage, http://www.planar.com/products/flatpanel_monitors/stereoscopic/ (Printed Dec. 29, 2011).
Keller et al., "What is it in Head Mounted Displays (MDs) that really make them all so terrible?," pp. 1-8 (1998).
Lee, et al., "Modeling Real Objects Using Video See-Through Augmented Reality," Proceedings of the Second International Symposium on Mixed Reality, ISMR 2001, pp. 19-26 (Mar. 14-15, 2001).
Symons et al., "What are You Looking at? Acuity for Triadic Eye Gaze," J. Gen. Psychology 131(4), pp. 451-469 (2004).
Takacs et al., "The Virtual Human Interface: A Photorealistic Digital Human," IEEE Computer Graphics and Applications 23(5), pp. 38-45 (2003).
Takayama et al., "Virtual Human with Regard to Physical Contact and Eye Contact," Entertaining Computing 2005, LNCS, vol. 3711, pp. 268-278 (2005).
U.S. Appl. No. 15/041,868, filed Feb. 11, 2016, Fuchs et al.
U.S. Appl. No. 15/068,323, filed Mar. 11, 2016, Razzaque et al.
U.S. Appl. No. 15/182,346, filed Jun. 14, 2016, Razzaque et al.
U.S. Appl. No. 15/199,630, filed Jun. 30, 2016, Razzaque et al.
U.S. Appl. No. 15/175,981, filed Jul. 7, 2016, Razzaque et al.
"Sony Introduces Head-Mounted Display for Endoscopic Surgery" (Jul. 23, 2013), retrieved Sep. 27, 2016, 5 pages, available at http://www.medgadget.com/2013/07/sony-introduces-head-mounted-display-for-endoscopic-surgery.html.
"Sony Introduces 'head-mount image processing unit' for endoscopic image display" (Jul. 23, 2013), retrieved Sep. 27, 2016, 14 pages, available at http://www.sony.net/SonyInfo/News/Press/201307/13-085E/index.html.
Agreements and Conferences Overview, various dates, 2 pages.
U.S. Appl. No. 15/415,398, filed Jan. 25, 2017, State et al., including its ongoing prosecution history, including without limitation Office Actions, Amendments, Remarks, and any other potentially relevant documents.
2017/0323424 including its ongoing prosecution history, including without limitation Office Actions, Amendments, Remarks, and any other potentially relevant documents.

(56) References Cited

OTHER PUBLICATIONS

Updated Agreements and Conferences Overview, various dates, 3 pages.
U.S. Pat. No. 9,901,406 including its ongoing prosecution history, including without limitation Office Actions, Amendments, Remarks, and any other potentially relevant documents.
U.S. Pat. No. 9,949,700 including its ongoing prosecution history, including without limitation Office Actions, Amendments, Remarks, and any other potentially relevant documents.
U.S. Appl. No. 15/799,639, filed Oct. 31, 2017, Green et al., including its ongoing prosecution history, including without limitation Office Actions, Amendments, Remarks, and any other potentially relevant documents.
U.S. Appl. No. 15/882,709, filed Jan. 29, 2018, Slate et al., including its ongoing prosecution history, including without limitation Office Actions, Amendments, Remarks, and any other potentially relevant documents.
U.S. Appl. No. 15/995,059, filed Apr. 17, 2018, Kohli et al., including its ongoing prosecution history, including without limitation Office Actions, Amendments, Remarks, and any other potentially relevant documents.
2017/0360395 including its ongoing prosecution history, including without limitation Office Actions, Amendments, Remarks, and any other potentially relevant documents.
2018/0116731 including its ongoing prosecution history, including without limitation Office Actions, Amendments, Remarks, and any other potentially relevant documents.
"AIM 3D Needle Placement Software from InnerOptic", Medgadget, Sep. 21, 2012.
"InnerOptic's AIM System Receives DA 510(K) Clearance", InnerOptic Technology, Inc., Sep. 18, 2012.
AIM, "Simple and Precise 3D Needle Guidance," in 2 pages, dated Aug. 2010. Applicant requests that the Examiner consider this reference as qualifying as prior art to the present application as of the date provided, but reserves the right to challenge the date of publication at a later time.
AIM, "Simple and Precise 3D Needle Guidance," in 2 pages, dated Feb. 2013. Applicant requests that the Examiner consider this reference as qualifying as prior art to the present application as of the date provided, but reserves the right to challenge the date of publication at a later time.
AIM, "Simple and Precise 3D Needle Guidance," in 2 pages, dated Mar. 2012. Applicant requests that the Examiner consider this reference as qualifying as prior art to the present application as of the date provided, but reserves the right to challenge the date of publication at a later time.
AIM, "Simple and Precise 3D Needle Guidance," in 2 pages, dated Mar. 2014. Applicant requests that the Examiner consider this reference as qualifying as prior art to the present application as of the date provided, but reserves the right to challenge the date of publication at a later time.
AIM, "Simple and Precise 3D Needle Guidance," in 2 pages, dated Oct. 2010. Applicant requests that the Examiner consider this reference as qualifying as prior art to the present application as of the date provided, but reserves the right to challenge the date of publication at a later time.
AIM, "Simple and Precise 3D Needle Guidance," in 2 pages, dated Sep. 2012. Applicant requests that the Examiner consider this reference as qualifying as prior art to the present application as of the date provided, but reserves the right to challenge the date of publication at a later time.
InVision InnerAim, "3D Visualization Software for a Simpler Safer, Precise Aiming," Brochure in 2 pages, Apr. 2010. Applicant requests that the Examiner consider this reference as qualifying as prior art to the present application as of the date provided, but reserves the right to challenge the date of publication at a later time.
InVision InnerOptic IVS Brochure, in 2 pages, Sep. 2008. Applicant requests that the Examiner consider this reference as qualifying as prior art to the present application as of the date provided, but reserves the right to challenge the date of publication at a later time.
InVision Section 5: 510(k) Summary, submitted by InnerOptic Technology, Inc., in 5 pages, submission date Dec. 15, 2008.
InVision System Brochure, A "GPS" for Real-time 3D Needle Guidance, in 2 pages, 2008. Applicant requests that the Examiner consider this reference as qualifying as prior art to the present application as of the date provided, but reserves the right to challenge the date of publication at a later time.
InVision System Brochure, A "GPS" for Real-time 3D Needle Guidance, in 2 pages, Jan. 2009. Applicant requests that the Examiner consider this reference as qualifying as prior art to the present application as of the date provided, but reserves the right to challenge the date of publication at a later time.
InVision System Brochure, A "GPS" for Real-time 3D Needle Guidance, in 2 pages, Jun. 2009. Applicant requests that the Examiner consider this reference as qualifying as prior art to the present application as of the date provided, but reserves the right to challenge the date of publication at a later time.
InVision System Brochure, A "GPS" for Real-time 3D Needle Guidance, in 2 pages, Oct. 2008. Applicant requests that the Examiner consider this reference as qualifying as prior art to the present application as of the date provided, but reserves the right to challenge the date of publication at a later time.
InVision System Brochure, A "GPS" for Real-time 3D Needle Guidance, in 2 pages, Sep. 2009. Applicant requests that the Examiner consider this reference as qualifying as prior art to the present application as of the date provided, but reserves the right to challenge the date of publication at a later time.
InVision System Needle Guidance Brochure, in 2 pages, 2008. Applicant requests that the Examiner consider this reference as qualifying as prior art to the present application as of the date provided, but reserves the right to challenge the date of publication at a later time.
InVision System Needle Guidance Brochure, in 2 pages, Aug. 2008. Applicant requests that the Examiner consider this reference as qualifying as prior art to the present application as of the date provided, but reserves the right to challenge the date of publication at a later time.
Lindeman, A Low-Cost, Low-latency Approach to Dynamic Immersion in Occlusive Head-Mounted Displays, University of Canterbury, WPI,—Poster from IEEE VR 2016, Mar. 19-23, 2016.
Ohnesorge, Lauren K., "InnerOptic technology wins FDA approval", Triangle Business Journal, Sep. 19, 2012.
Press Release: Pathfinder and InnerOptic Announce Technology Integration to Enhance Visualization and Outcomes in Liver Surgery, Published Mar. 6, 2013.
AIM Section 5: 510(k) Summary, submitted by InnerOptic Technology, Inc., in 5 pages, submission date May 17, 2012.

* cited by examiner

MEDICAL DEVICE GUIDANCE

CROSS-REFERENCE TO RELATED APPLICATIONS

The present application claims priority benefit to U.S. Provisional Application No. 61/783,044, filed Mar. 14, 2013, which is hereby incorporated herein by reference in its entirety.

TECHNICAL FIELD

The systems and methods disclosed herein relate generally to computer systems facilitating medical device guidance through tissue by a medical practitioner.

BACKGROUND

Various medical device systems are available to aid a healthcare provider to guide a medical device in a patient. The medical device systems can provide various image guidance cues to aid the healthcare provider, and can also provide views of images of an imaged area and of virtual medical devices corresponding to physical medical devices. Unfortunately, in some instances, the orientation of the view, as well as a point-of-view location, are fixed and cannot be changed by the user. In addition, systems that display image guidance elements often display a translucent medical image so that any guidance elements located behind the medical image can be seen. However, by decreasing the opacity (and the image intensity and contrast) of the medical image, it can be more difficult for the healthcare provider to identify important features in the medical image. In addition, when image guidance cues are co-located with medical display object on the display, the medical device system may switch between displaying the image guidance cue and the medical display object, resulting in a flicker.

DETAILED DESCRIPTION

Figure 1:
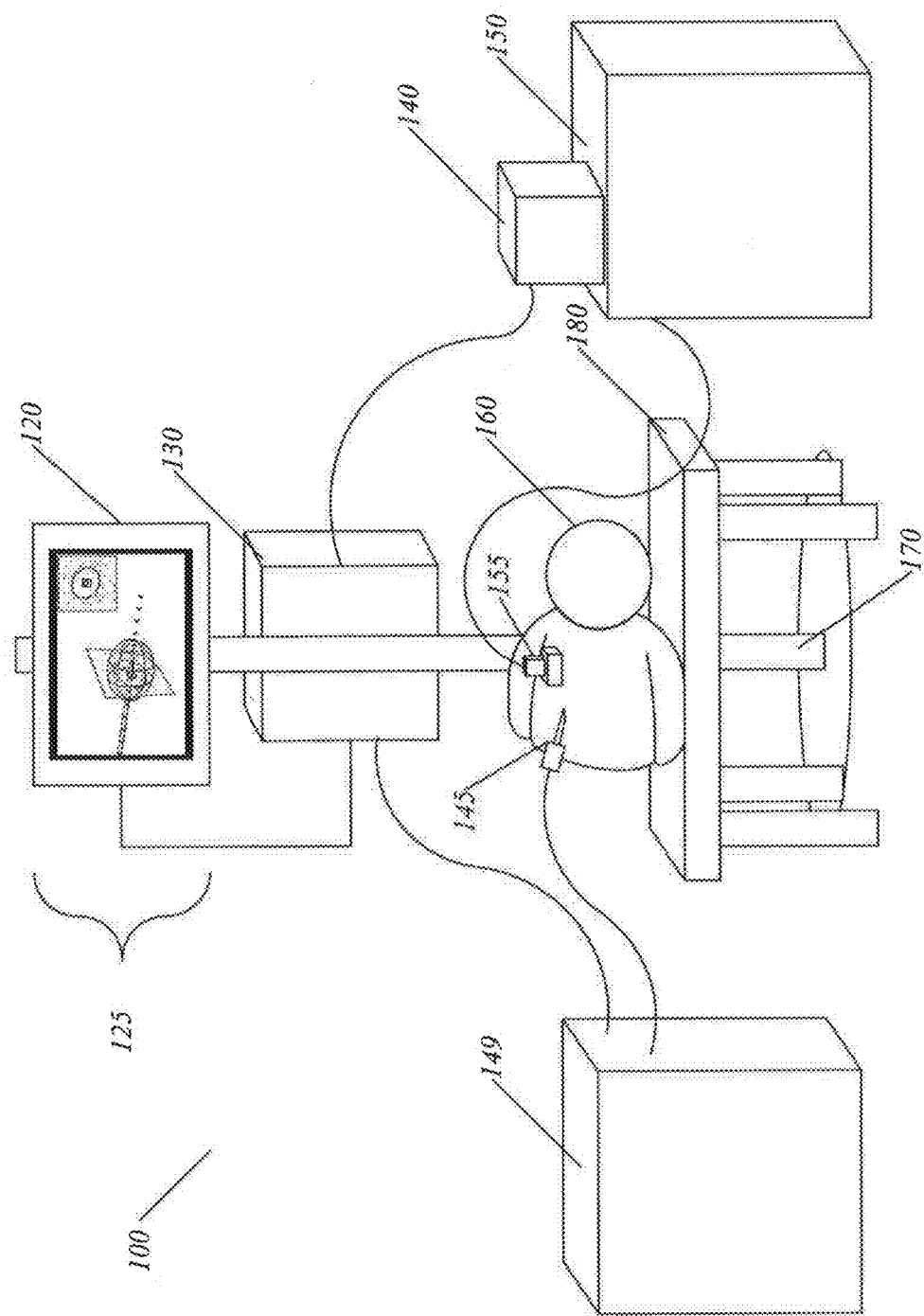
FIG. 1 is a diagram of an embodiment of a system for image-guided medical procedures.

Implementations disclosed herein provide systems, methods and apparatus for generating images facilitating medical device insertion into tissue by an operator. Certain embodiments pertain to a free-hand medical device guidance system. The system can provide the healthcare provider manual control over the medical device, while making the spatial relationships between the target, medical device and U/S image more intuitive via a visual display. Using this visual feedback, the operator can adjust the medical device's position, orientation, or trajectory. Certain of the contemplated embodiments can be used in conjunction with systems described in greater detail in U.S. patent application Ser. No. 13/014,587, filed Jan. 26, 2011, entitled SYSTEMS, METHODS, APPARATUSES, AND COMPUTER-READABLE MEDIA FOR IMAGE MANAGEMENT IN IMAGE-GUIDED MEDICAL PROCEDURES and U.S. patent application Ser. No. 13/753,274, filed Jan. 29, 2013, entitled MULTIPLE MEDICAL DEVICE GUIDANCE (the '274 application), each of which is hereby incorporated by reference in its entirety.

The system can aid the healthcare provider in guiding one or more medical devices through the tissue of the patient and/or placing the medical devices, and can be used for treatment of tumors, fibroids or cysts, with bipolar radiofrequency medical device ablation, multiple microwave medical devices, electroporation, and/or electrochemotherapy systems. It can also be used for nerve or muscle stimulation or sensing (electrodes in the spine, brain). The system can be used during open surgery, laparoscopic surgery, endoscopic procedures, biopsies, and/or interventional radiology procedures.

The system can be used in conjunction with live intraoperative ultrasound (U/S), pre-operative CT, or any cross-sectional medical imaging modality (e.g. MRI, OCT, etc.). In addition, the system can use a variety of techniques to determine the position and/or orientation of one or more medical devices. For example, the system can use the NDI Aurora magnetic system, NDI Polaris optical system, etc. In some embodiments, a position sensor can be embedded inside, or affixed to each medical device, at the tip, along the shaft, or on the handle. Sensors can be built into the medical devices or attached after manufacturing, as described in greater detail in U.S. application Ser. No. 14/212,184, filed Mar. 14, 2014, entitled SENSOR MOUNT, incorporated herein in its entirety.

Each medical device can be associated with one or more sensors, which continually report position and/or orientation, or a single sensor can be used for all the medical devices. In embodiments where one sensor is used, the healthcare provider can attach the sensor to the particular medical device that she is intentionally repositioning, and then, once she has placed that medical device, she would remove the sensor and attach it to the next medical device she is repositioning. In some embodiments, the medical devices, U/S probe and/or laparoscope can be manipulated by the healthcare provider. In certain embodiments, the system can be used with a robotic manipulator, where the robot controls the medical devices, U/S probe and/or laparoscope.

In some embodiments, the handles of medical devices can have push-button switches, to allow the user to select a medical device, indicate a tissue target, etc. The handle can also have an indicator light to indicate to the users which medical device is selected. Finally, the handle can have an encoder to detect how much length of electrode has been exposed by the user, and report this information to the guidance system and therapeutic generator Image Guidance Systems FIG. 1 is a diagram illustrating an embodiment of a system for image management in image-guided medical procedures. In some embodiments, the position sensing unit 140 can track surgical instruments, also referred to herein as medical devices, within a tracking area and provide data to the image guidance unit 130. The medical devices can include invasive medical devices, biopsy needles, ablation needles, surgical needles, nerve-block needles, or other needles, electrocautery device, catheters, stents, laparoscopic cameras, or other instruments that enter a part of the body, and non-invasive medical devices that do not enter the body, such as ultrasound transducers. The medical devices can also include medical imaging devices that provide or aid in the selection of medical images for display. In some embodiments, the medical imaging device can be any device that is used to select a particular medical image for display. The medical imaging devices can include invasive medical devices, such as laparoscopic cameras, and non-invasive medical devices, such as ultrasound transducers.

Although only two surgical instruments 145 and 155 are shown in FIG. 1, it will be understood that additional surgical instruments can be tracked and associated data can be provided to the image guidance unit 130. The image guidance unit 130 can process or combine the data and show image guidance data on display 120. This image guidance data can be used by a healthcare provider to guide a procedure and improve care. There are numerous other possible embodiments of system 100. For example, many of the depicted modules can be joined together to form a single module and can be implemented in a single computer or machine. Further, additional position sensing units can be used in conjunction with position sensing unit 140 to track all relevant surgical instruments 145 and 155, as discussed in more detail below. Additional imaging units 150 can be included, and combined imaging data from the multiple imaging units 150 can be processed by image guidance unit 130 and shown on display unit 120. Additionally, two or more surgical systems 149 can also be included.

Information about and from multiple surgical systems 149 and attached surgical instruments 145 (and additional surgical instruments not shown) can be processed by image guidance unit 130 and shown on display 120. These and other possible embodiments are discussed in more detail below.

Imaging unit 150 can be coupled to image guidance unit 130. In some embodiments, imaging unit 150 can be coupled to a second display unit (not shown). The second display unit can display imaging data from imaging unit 150. The imaging data displayed on display unit 120 and displayed on second display unit can be the same or different. In some embodiments, the imaging unit 150 is an ultrasound machine 150, the movable imaging device 155 is an ultrasound transducer 155 or ultrasound probe 155, and the second display unit is a display associated with the ultrasound machine 150 that displays the ultrasound images from the ultrasound machine 150. In some embodiments, a movable imaging unit 155 can be connected to image guidance unit 130. The movable imaging unit 155 can be useful for allowing a user to indicate what portions of a first set of imaging data are to be displayed. For example, the movable imaging unit 155 can be an ultrasound transducer 155, a needle or other medical device, for example, and can be used by a user to indicate what portions of imaging data, such as a pre-operative CT scan, to show on a display unit 120 as image 125. Further, in some embodiments, there can be a third set of pre-operative imaging data that can be displayed with the first set of imaging data.

In some embodiments, system 100 comprises a display unit 120 and a position sensing unit 140 communicatively coupled to image guidance unit 130. In some embodiments, position sensing unit 140, display unit 120, and image guidance unit 130 are coupled to the stand 170. Image guidance unit 130 can be used to produce images 125 that are displayed on display unit 120. The images 125 produced on display unit 120 by the image guidance unit 130 can be determined based on ultrasound or other visual images from the first surgical instrument 145 and second surgical instrument 155.

For example, if the first surgical instrument 145 is an ablation needle 145 and the second surgical instrument 155 is an ultrasound probe 155, then images 125 produced on display 120 can include the images, or video, from the ultrasound probe 155 combined with other medical display objects and image guidance cues, such as projected medical device drive (e.g., trajectory indicators) or projected ablation volume (e.g., ablation zone indicators), determined based on the emplacement of ablation needle 145. If the first surgical instrument 145 is an ultrasound probe 145 and the second surgical instrument 155 is a laparoscopic camera 155, then images 125 produced on display 120 can include the video from the laparoscopic camera 155 combined with ultrasound data superimposed on the laparoscopic image. More surgical instruments can be added to the system. For example, the system can include an ultrasound probe, ablation needle, laparoscopic camera, stapler, cauterizer, scalpel and/or any other surgical instrument or medical device. The system can also process and/or display collected data, such as preoperative CT scans, X-Rays, MRIs, laser scanned 3D surfaces etc.

The term "emplacement" and the term "pose" as used herein are broad terms encompassing their plain and ordinary meanings and may refer to, without limitation, position and/or orientation, the combination of position and orientation, or any other appropriate location information. In some embodiments, the imaging data obtained from one or both of surgical instruments 145 and 155 can include other modalities such as a CT scan, MRI, open-magnet MRI, optical coherence tomography ("OCT"), positron emission tomography ("PET") scans, fluoroscopy, ultrasound, or other preoperative, or intraoperative 2D or 3D anatomical imaging data. In some embodiments, surgical instruments 145 and 155 can also be scalpels, implantable hardware, or any other device used in surgery. Any appropriate surgical system 149 or imaging unit 150 can be attached to the corresponding medical instruments 145 and 155.

As noted above, images 125 produced can also be generated based on live, intraoperative, or real-time data obtained using the second surgical instrument 155, which is coupled to second imaging unit 150. The term "real time" as used herein is a broad term and has its ordinary and customary meaning, including without limitation instantaneously or nearly instantaneously. The use of the term real time can also mean that actions are performed or data is obtained with the intention to be used immediately, upon the next cycle of a system or control loop, or any other appropriate meaning. Additionally, as used herein, real-time data can be data that is obtained at a frequency that would allow a healthcare provider to meaningfully interact with the data during surgery. For example, in some embodiments, real-time data can be a medical image of a patient that is updated one time per second. In some embodiments, real-time data can be ultrasound data that is updated multiple times per second.

The surgical instruments 145, 155 can be communicatively coupled to the position sensing unit 140 (e.g., sensors embedded or coupled to the surgical instruments 145, 155 can be communicatively coupled with the position sensing unit 140). The position sensing unit 140 can be part of imaging unit 150 or it can be separate. The position sensing unit 140 can be used to determine the emplacement of first surgical instrument 145 and/or the second surgical instrument 155. In some embodiments, the position sensing unit 140 can include a magnetic tracker and/or one or more magnetic coils can be coupled to surgical instruments 145 and/or 155. In some embodiments, the position sensing unit 140 can include an optical tracker and/or one or more visually-detectable fiducials can be coupled to surgical instruments 145 and/or 155. In some embodiments, the position sensing unit 140 can be located below the patient. In such embodiments, the position sensing unit 140 can be located on or below the table 180. For example, in embodiments where the position sensing unit 140 is a magnetic tracker, it can be mounted below the surgical table 180. Such an arrangement can be useful when the tracking volume of the position sensing unit 140 is dependent on the location of the position sensing unit, as with many magnetic trackers. In some embodiments, magnetic tracking coils can be mounted in or on the medical devices 145 and 155.

In some embodiments, the position sensing unit 140 can be an electromagnetic measurement system (e.g., NDI Aurora system) using sensor coils for tracking units attached to the first and/or second surgical devices 145 and 155. In some embodiments, the second position sensing unit 140 can be an optical 3D tracking system using fiducials. Such optical 3D tracking systems can include the NDI Polaris Spectra, Vicra, Certus, PhaseSpace IMPULSE, Vicon MX, InterSense IS-900, NaturalPoint OptiTrack, Polhemus FastTrak, IsoTrak, or Claron MicronTracker2. In some embodiments, the position sensing unit 140 can each be an inertial 3D tracking system comprising a compass, accelerometer, tilt sensor and/or gyro, such as the InterSense InertiaCube or the Nintendo Wii controller. In some embodiments, the position sensing unit 140 can be attached to or affixed on the corresponding surgical device 145 and 155.

In some embodiments, the position sensing units 140, can include sensing devices such as the HiBall tracking system, a GPS device, or signal emitting device that would allow for tracking of the position and/or orientation (e.g., pose) of the tracking unit (also referred to as a pose sensor). In some embodiments, a position sensing unit 140 can be affixed to either or both of the surgical devices 145 and 155. The surgical devices 145 or 155 can be tracked by the position sensing unit 140. A room coordinate system reference, such as the display 120 can also be tracked by the position sensing unit 140 in order to determine the emplacements of the surgical devices 145 and 155 with respect to the room coordinate system. Devices 145 and 155 can also include or have coupled thereto one or more accelerometers, which can be used to estimate movement, position, and location of the devices.

In some embodiments, the position sensing unit 140 can be an Ascension Flock of Birds, Nest of Birds, driveBAY, medSAFE, trakSTAR, miniBIRD, MotionSTAR, pciBIRD, or Calypso 2D Localization System and tracking units attached to the first and/or second medical devices 145 and 155 can be magnetic tracking coils.

The term "tracking unit" (also referred to as a pose sensor), as used herein, is a broad term encompassing its plain and ordinary meaning and includes without limitation all types of magnetic coils or other magnetic field sensing devices for use with magnetic trackers, fiducials or other optically detectable markers for use with optical trackers, such as those discussed above and below. In some embodiments, the tracking units can be implemented using optical position sensing devices, such as the HiBall tracking system and the position sensing unit 140 can form part of the HiBall tracking system. Tracking units can also include a GPS device or signal emitting device that allows for tracking of the position and/or orientation of the tracking unit. In some embodiments, a signal emitting device might include a radio-frequency identifier (RFID). In such embodiments, the position sensing unit 140 can use the GPS coordinates of the tracking units or can, for example, triangulate the radio frequency signal being emitted by the RFID associated with tracking units. The tracking systems can also include one or more 3D mice.

Images 125 can be produced based on intraoperative or real-time data obtained using first surgical instrument 145, which is coupled to first surgical system 149. In the illustrated embodiment of FIG. 1, the first surgical system 149 is shown as coupled to image guidance unit 130. The coupling between the first surgical system 149 and image guidance unit 130 may not be present in all embodiments. In some embodiments, the coupling between first surgical system 149 and image guidance unit 130 can be included where information about first surgical instrument 145 available to first surgical system 149 is useful for the processing performed by image guidance unit 130. For example, in some embodiments, the first surgical instrument 145 is an ablation needle 145 and first surgical system 149 is an ablation system 149. In some embodiments, it can be useful to send a signal about the relative strength of planned ablation from ablation system 149 to image guidance unit 130 in order that image guidance unit 130 can show a predicted ablation volume. In other embodiments, the first surgical system 149 is not coupled to image guidance unit 130. Example embodiments including images and graphics that can be displayed are included below.

In some embodiments, the display unit 120 displays 3D images to a user, such as a healthcare provider. Stereoscopic 3D displays separate the imagery shown to each of the user's eyes. This can be accomplished by a stereoscopic display, a lenticular auto-stereoscopic display, or any other appropriate type of display. The display 120 can be an alternating row or alternating column display. Example alternating row displays include the Miracube G240S, as well as Zalman Trimon Monitors. Alternating column displays include devices manufactured by Sharp, as well as many "auto-stereoscopic" displays (e.g., Philips). In some embodiments, Sony Panasonic 3D passive displays and LG, Samsung, and/or Vizio 3D TVs can be used as well. Display 120 can also be a cathode ray tube. Cathode Ray Tube (CRT) based devices, can use temporal sequencing, showing imagery for the left and right eye in temporal sequential alternation. This method can also be used projection-based devices, as well as by liquid crystal display (LCD) devices, light emitting diode (LED) devices, and/or organic LED (OLED) devices.

In certain embodiments, a user can wear a head mounted display in order to receive 3D images from the image guidance unit 130. In such embodiments, a separate display, such as the pictured display unit 120, can be omitted. The 3D graphics can be produced using underlying data models, stored in the image guidance unit 130 and projected onto one or more 2D planes in order to create left and right eye images for a head mount, lenticular, or other 3D display. The underlying 3D model can be updated based on the relative emplacements of the various devices 145 and 155, as determined by the position sensing unit(s), and/or based on new data associated with the devices 145 and 155. For example, if the second medical device 155 is an ultrasound probe, then the underlying data model can be updated to reflect the most recent ultrasound image. If the first medical device 145 is an ablation needle, then the underlying model can be updated to reflect any changes related to the needle, such as power or duration information. Any appropriate 3D graphics processing can be used for rendering including processing based on OpenGL, Direct3D, Java 3D, etc. Whole, partial, or modified 3D graphics packages can also be used, such packages including 3DS Max, SolidWorks, Maya, Form Z, Cybermotion 3D, VTK, Slicer, or any others. In some embodiments, various parts of the needed rendering can occur on traditional or specialized graphics hardware. The rendering can also occur on the general CPU, on programmable hardware, on a separate processor, be distributed over multiple processors, over multiple dedicated graphics cards, or using any other appropriate combination of hardware or technique.

One or more modules, units, devices, or elements of various embodiments can be packaged and/or distributed as part of a kit. For example, in one embodiment, an ablation needle, one or more tracking units, 3D viewing glasses, and/or a portion of an ultrasound wand can form a kit. Other embodiments can have different elements or combinations of elements grouped and/or packaged together. Kits can be sold or distributed separately from or with the other portions of the system.

One will readily recognize that there are numerous other examples of image guidance systems which can use, incorporate, support, or provide for the techniques, methods, processes, and systems described herein.

Depicting Surgical Instruments

It can often be difficult to discern the content of a 3D scene from a 2D depiction of it, or even from a 3D depiction of it. Therefore, various embodiments herein provide image guidance that can help the healthcare provider better understand the scene, relative emplacements or poses of object in the scene and thereby provide improved image guidance.

Figure 2:
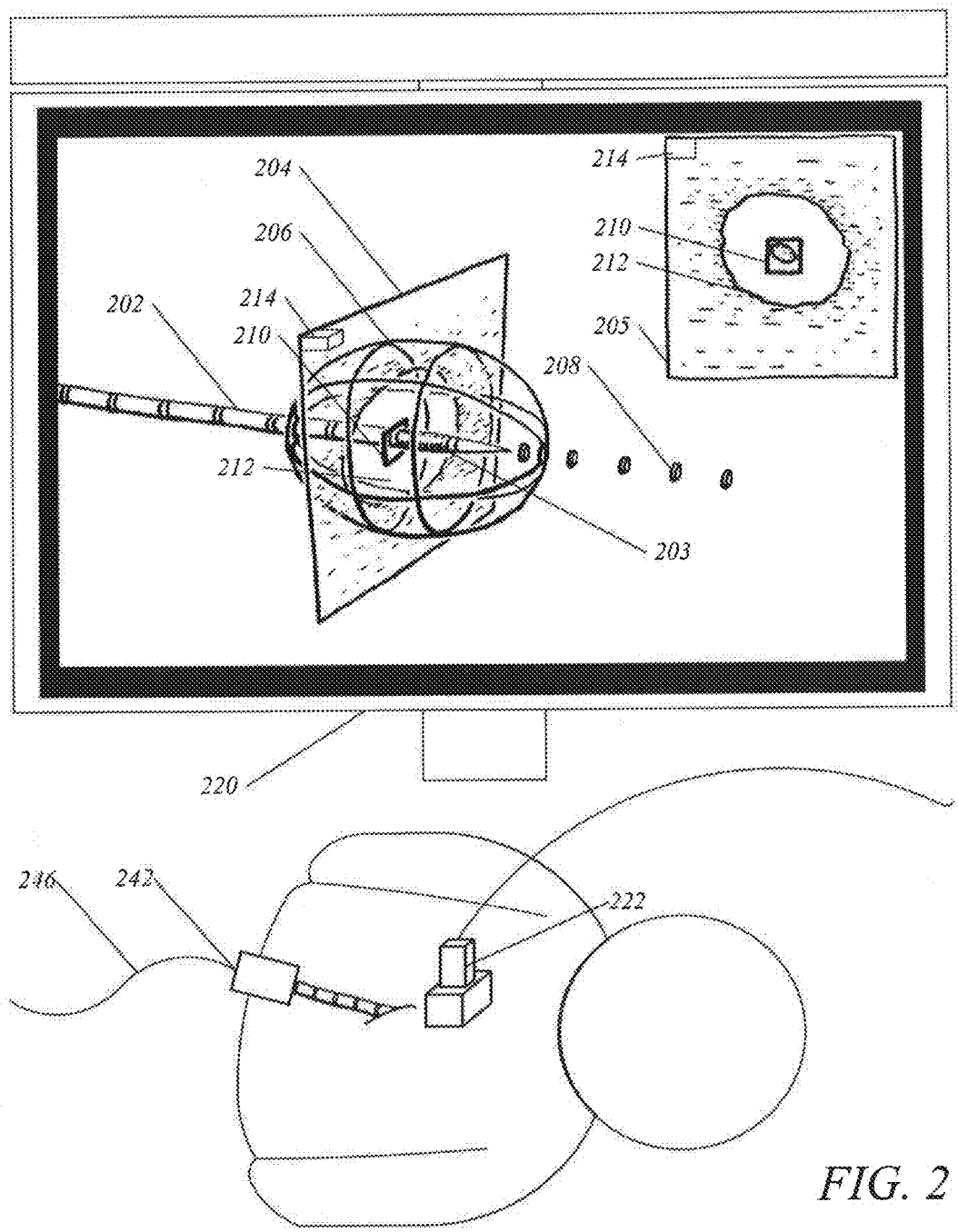
FIG. 2 is a diagram of an embodiment of a rendering of image guidance cues and medical display objects on a display.

FIG. 2 illustrates a perspective view of a virtual rendering 202 of a surgical instrument 242 being displayed on a screen 220 with a perspective view of a medical image 204. In this case, the rendered surgical instrument 202 displayed is an ablation needle 242. A wire 246 connecting the ablation needle 242 to an ablation system is also depicted. Although only one virtual surgical instrument 202 is displayed, it will be understood that multiple medical devices can be tracked and displayed simultaneously on screen 220, as described in greater detail in the '274 application, previously incorporated by reference. For example, a virtual rendering of the medical imaging device that corresponds to the medical image 204 can be displayed.

The virtual surgical instrument 202 can be displayed in a virtual 3D space with the screen 220 acting as a window into the virtual 3D space. Thus, as the surgical instrument 242 is moved to the right with respect to a point-of-view location (e.g., the location of the point-of-view for viewing the 3D space), the virtual surgical instrument 202 also moves to the right. Similarly, if the surgical instrument 242 is rotated 90 degrees so that the tip of the surgical instrument is pointing away from the point-of-view location (e.g., at the screen 220), the virtual surgical instrument 201 will likewise show the change in orientation, and show the tip of the virtual surgical instrument 202 in the background and the other end of the virtual surgical instrument 202 in the foreground.

Some models of medical devices have markings such as bands around the shaft (to indicate distance along the shaft), and a colored region 203 near the tip to indicate from where the radio frequency or microwave energy is emitted in the case of an ablation probe. Healthcare providers performing medical device procedures are often familiar with these markings and can use them to help understand the spatial relationship between the medical device and anatomy. In some embodiments, the make and model of the medical device 242 is known to the image guidance system and the virtual medical device displayed (202) in display 220 can resemble medical device 242. The features of medical devices that can be rendered in the scene include the overall shape (diameter, cross sectional shape, curvature, etc.), color, distance markers, visuals or echogenic fiduciary markers, the state of deployable elements such as tines, paddles, anchors, resection loops, stiffening or steerable sleeves, temperature, radiation, light or magnetic field sensors, lens, waveguides, fluid transfer channels, and the like.

The type of medical device being used can be input into the image guidance system 100, can be a system default, can be detected by a camera or other device, can be received as data from an attached medical device, such as surgical system 149 in FIG. 1, or the information can be received in any other appropriate manner. Displaying on display 220, a virtual surgical instrument that resembled the surgical instrument 242 can help healthcare providers associate the image guidance data with the real world and can provide more familiar guidance information to a healthcare provider, thereby further aiding the healthcare provider in the guidance task. For example, the healthcare provider can see the familiar markings on the medical device being displayed on the display 220 and therefore be familiar with the distance and relative placement of the displayed medical device with respect to other data, such as a tumor 212 seen in a rendered ultrasound image 204, 205. This knowledge of relative placement of items being displayed can help the healthcare provider move the medical device into place.

Consider an embodiment in which the virtual surgical instrument 202 in the display 220 is an ablation needle depicting the portion of the needle that will perform the ablation, for example, the portion that emits the radio or microwave energy. If the display 220 also includes ultrasound data, then the doctor can be able to find the tumor 212 she wishes to ablate by moving the ultrasound probe around until she spots the tumor 212. In various embodiments, she will be able to see the displayed ultrasound data and its location relative to the displayed medical device with the markings. She can then drive the medical device until she sees, on display 220, that the emitter-portion of the medical device encompasses the tumor in the ultrasound, also seen on display 220. When she activates the ablation, she can then be much more certain that she has ablated the correct portion of the tissue. Various embodiments of this are discussed below.

As another example, consider the physical markings that can be on the instruments themselves. These markings can help orient a healthcare provider during use of the instrument. In some embodiments, the image guidance unit can represent these markings in the images displayed in the display. For example, certain ultrasound transducers are built with an orientation mark (e.g., a small bump) on one side of the transducing array. That mark can also be shown in the ultrasound image on the scanner's display, to help the healthcare provider understand where the scanned anatomical structures shown on screen are located under the transducer, inside the patient. In some embodiments, the image guidance system can display a symbolic 3D representation of the orientation mark both next to the motion-tracked ultrasound slice (e.g., moving with the displayed ultrasound slice) and next to the 2D ultrasound slice also displayed by the system. An example of this is displayed in FIG. 2, where a small rectilinear volume 214 corresponding to a feature on an ultrasound probe is shown both in proximity to the ultrasound slice displayed in 3D and the ultrasound slice displayed as a 2D image.

Other embodiments can track and display other types of instruments and their features. For example, a healthcare provider may want to track one or more of a scalpel, a biopsy, a cauterizer (including an electrocauterizer and Bovies), forceps, cutting loops on hysteroscopes, harmonic sheers, lasers (including $CO_2$ lasers), etc. For example, in various embodiments, the following devices can be tracked and various aspects of their design displayed on display 220: Olympus™ OES Pro Hystero-Resectoscope, SonoSurg Ultrasonic Surgical System Olympus™ GF-UC 160 Endoscope Wallus™ Embryo Transfer Catheter AngioDynamics® NanoKnife™, VenaCure™ laser, StarBurst, Uniblade, Habib® Resector Bovie™ Electrodes, Covidien Evident™, Cool-Tip™ Ablation Antennas, Opti4™ Electrodes Microsulis MEA (microwave endometrial ablation), Acculis Halt™ Medical System Optimed BigLumen Aspiration Catheter Optimed Optipure Stent Central venous catheterization introducer medical device (such as those made by Bard and Arrow).

Once tracked, a healthcare provider is able to see image guidance data on display 220 that will allow her to know the relative pose, location, or emplacement of the tracked instrument(s) with respect to one another or with respect to imaging data and will be able to see, on display 220, the features of the instrument rendered in the scene.

Depicting Ablation Volume and Other Information

Various embodiments of the system can depict information related to the surgical instruments, such as image guidance cues, as part of the image guidance data. For example, in some embodiments, an image guidance cue displayed by the image guidance system can include an expected spherical ablation volume. For example, FIG. 2 shows a virtual ablation needle 202 which has a darkened portion 203 that indicates where the radio frequency or microwave energy for ablation will be emitted. In some embodiments, an image guidance system can display on display 220 the expected ablation volume 206. The ablation volume 206 can be shown as a transparent volume, a wireframe volume (as depicted in FIG. 2), as a point cloud of various densities, as an outline, as a volume, or in any other appropriate manner. Although only one ablation volume 206 is displayed, it will be understood that multiple ablation volumes can be displayed for each medical device 242 that is displayed on the screen 220.

For some ablation needles, the expected volume of ablated tissue is neither spherical nor centered at the tip of the medical device. For example, a Covidien surgical microwave medical device has an ellipsoidal ablation volume; a Covidien Evident transcutaneous microwave medical device has a teardrop-like ablation volume; RFA Medical's bipolar ablation system uses two medical devices simultaneously, where each medical device has paddles that deploy after the medical device is inserted inside the tissue (which one can equate to a canoe's oar). In some embodiments, the ablation volume for such a medical device is, to a first approximation, a volume that lies directly between the paddles of the two medical devices.

The pose of the volume can be specified by the placement of a tracked medical device, such as medical device 242 in FIG. 2. In some embodiments, with single medical device ablation systems, the volume's approximate size (e.g., girth and length, if ellipsoidal) can be either specified by the healthcare provider, or automatically computed by the guidance system. The ablation volume 206 can be based on numerous parameters such as the medical device make and model, power and duration settings of the microwave or radio frequency generator, measured or estimated temperature and impedance of the target tissue or other tissue information, a formula, a look-up-table, fixed or default values, or based on any other appropriate available information.

Other instrument information can also be depicted. For example, if a cauterizer is tracked as part of an image guidance system, then the cauterization volume can be determined or estimated and that volume can be displayed. If a laser is tracked as part of the image guidance system, then the projected laser path can be determined or estimated and displayed. In embodiments where multiple medical devices are used, the combined volume can be shown, as described in greater detail in the '274 application.

Depicting Medical Device Placement, Trajectory, and Other Image Guidance Cues

In certain procedures, the system can provide image prediction information related to the surgical instruments as image guidance cues. In the context of scalpel movement, this can be the location that the scalpel will hit if a healthcare provider continues to move the scalpel in a particular direction. In the context of ablation or biopsies, this can be the projected medical device placement if it is driven along its central axis, which is also referred to herein as a longitudinal axis.

FIG. 2 further illustrates an embodiment of a projected needle drive 208 (also referred to as a trajectory indicator) as an image guidance cue. If a healthcare provider is driving an ablation needle 242 into tissue (not pictured), then she can know where the medical device will be driven. In some embodiments, the projected drive 208 of a medical device can be depicted on the display 220 and can show the healthcare provider the projected path 208 that the medical device 242 will take if it is driven along its central axis. Although the trajectory of only one medical device is displayed, it will be understood that the trajectory of multiple medical devices can be determined and displayed simultaneously on screen 220, as described in greater detail in the '274 application.

Figure 4:
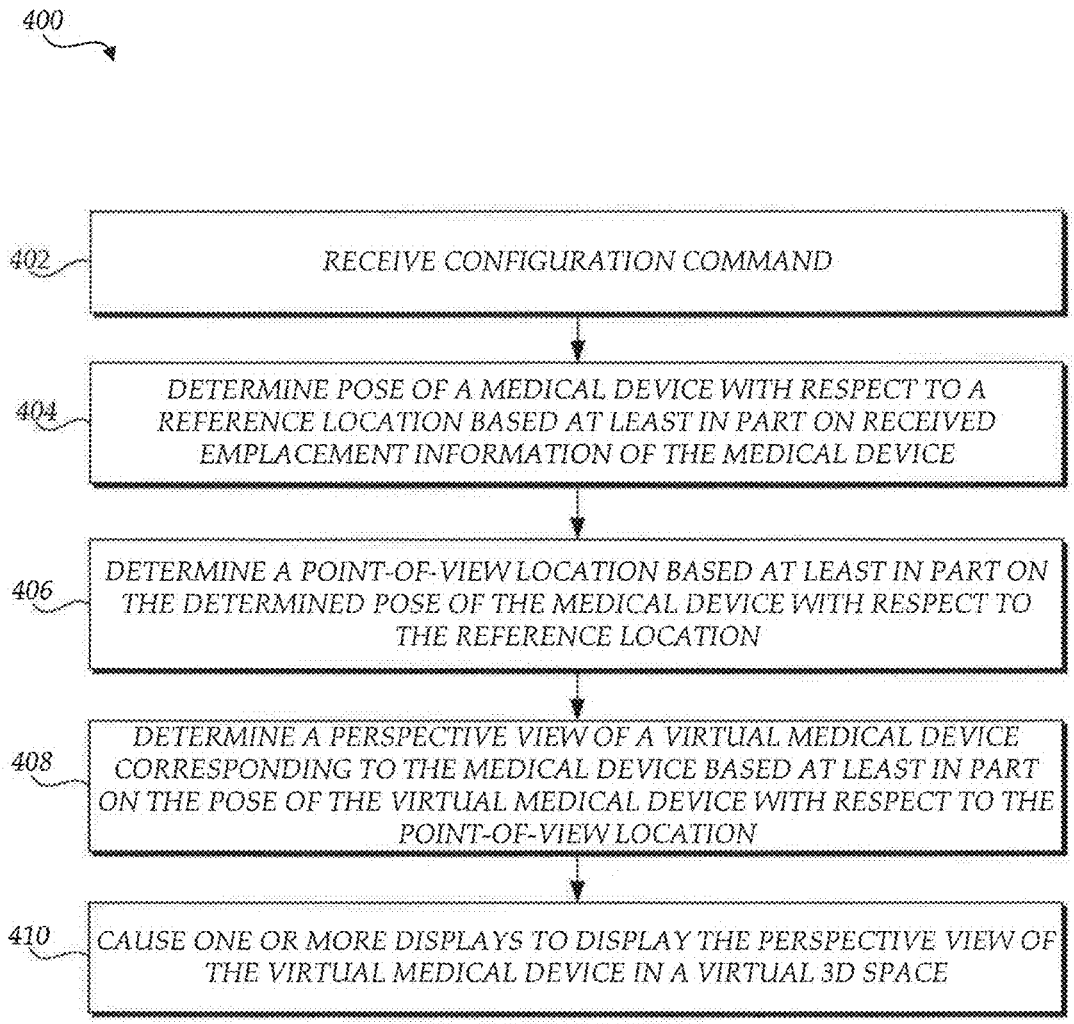
FIG. 4 is a flow diagram illustrative of an embodiment of a routine implemented by the system to configure a point-of-view location.

In some embodiments, to implement the trajectory indicators 208, the image guidance system can draw a number of rings about the axis of the medical device shaft, extrapolated beyond its tip, as depicted in FIG. 4. A healthcare provider can view and manipulate the pose of the medical device 242 and its expected drive projection (via its displayed projected trajectory) before it enters the patient's tissue. In some embodiments, this is accomplished by the doctor positioning the virtual rings in the drive projection such that they are co-incident (or pass through) the ultrasound representation of a target, such as a tumor that the doctor has spotted in the ultrasound. This can allow the healthcare provider to verify that the medical device 242 is properly aimed at the target and can drive the medical device 242 forward into the tissue such that it reaches its desired target or destination. For example, if the doctor identifies a tumor 212 in the ultrasound image, she can align the ablation needle 242 such that the drive projection rings on display 220 intersect or otherwise indicate that the medical device, if driven straight, will reach the tumor 212.

The rings can be spaced at regular (e.g., 0.5, 1, or 2 cm) intervals to provide the healthcare provider with visual or guidance cues regarding the distance from the medical device tip to the targeted anatomy. In some embodiments, the spacing of the rings can indicate other aspects of the data, such as the drive speed of the medical device, the density of the tissue, the distance to a landmark, such as the ultrasound data, or any other appropriate guidance data or property. In some embodiments, the rings or other trajectory indicators can extend beyond the medical device tip, by a distance equal to the length of the medical device-shaft. This way, the user knows if the medical device is long enough to reach the target—even before the tip enters the patient. That is, in some embodiments, if the rings do not reach the target with the tip still outside the body, then the tip won't reach the target even when the entire length shaft is inserted into the body.

Other display markers can be used to show trajectory, such as a dashed, dotted, or solid line, transparent medical device shaft, point cloud, wire frame, etc. In some embodiments, three-dimensional rings can be used and provide depth cues and obscure little of the ultrasound image. Virtual rings or other virtual markers can be displayed semi-transparently, so that they obscure less of the ultrasound image than an opaque marker would.

Other prediction information can also be displayed as image guidance cues. For example, if a scalpel is being tracked by the image guidance system, then a cutting plane corresponding to the scalpel can be displayed (not pictured). Such a cutting plan can be coplanar with the blade of the scalpel and can project from the blade of the scalpel. For example, the projected cutting plane can show where the scalpel would cut if the doctor were to advance the scalpel. Similar prediction information can be estimable or determinable for cauterizers, lasers, and numerous other surgical instruments.

Furthermore, the data from two or more devices can be combined and displayed based on their relative emplacements or poses. For example, the system 100 can determine an image plane based on the emplacement information of the ultrasound probe 222. Further, the rendered ultrasound image 204 can be displayed on the image plane with respect to the virtual medical device 202 on the display 220 in a manner that estimates the relative emplacements or poses of an ultrasound probe 222 and the medical device 242. As illustrated in FIG. 2, the image guidance cues associated with the virtual medical 202, including the ablation volume indicator 206 and trajectory indicators 208, are shown spatially located with the rendered ultrasound image 204 on display 220.

In addition, the display 220 includes another image guidance cue in the form of an intersection indicator 210 that indicates the where the virtual ablation medical device 202 intersects the ultrasound image 204. In some embodiments, the intersection indicator 210 can be displayed before the medical device is inserted, thereby allowing the healthcare provider to see where the medical device will intersect the image, or imaged area.

In the illustrated embodiment, a tumor 212 appears in the ultrasound image, or rendered ultrasound image 204, and the virtual ablation needle 202 is shown driven through the tumor 212. The ablation volume 206 estimates where ablation would occur if the tissue were ablated at that time. The healthcare provider can see that the ablation volume 206 appears to cover the tumor displayed in the ultrasound image.

Various embodiments can include any combinations of the graphics described above and/or other graphics or image guidance cues. For example, in some embodiments, data related to a single surgical instrument (such as an ablation needle, ultrasound probe, etc.) can be presented in more than one manner on a single display. Consider an embodiment in which device 242 is an ablation needle and device 222 is an ultrasound transducer. As mentioned previously, as the medical devices are displayed in a virtual 3D space, with the screen 220 acting as a window into the virtual 3D space, if a healthcare provider orients ultrasound transducer 222 such that it is perpendicular to the point-of-view or point-of-view location (e.g., perpendicular to the screen), the perspective view of the ultrasound image 204 would show only the edge and the contents of the ultrasound image 204 would not be visible. In some embodiments, the image guidance system can track the healthcare provider's head using a pose sensor and/or a position sensing unit. In some embodiments, such as, when the head of a user is tracked, the healthcare provider can then move her head to the side, so that she sees the ultrasound image from a different point of view location.

In some embodiments, the image guidance system can constantly display an additional 2D view 205 of the ultrasound image, simultaneous to the 3D depiction 204, so that the ultrasound image is always visible, regardless of the pose in which the healthcare provider holds the transducer 222. The 2D image 205 of the ultrasound data can be similar to what a healthcare provider is accustomed to seeing with traditional ultrasound displays. This can be useful to provide the healthcare provider with imaging to which she is accustomed and allows a healthcare provider to see the ultrasound data regardless of the then-current pose of the ultrasound probe with respect to the user.

In some embodiments, the 2D view 205 of an ultrasound image is depicted in the upper right corner of the monitor (though it can be placed in any location). In some embodiments, the guidance system can automatically (and continually) choose a corner in which to render the 2D view 205 of the ultrasound image, based on the 3D position of the surgical instruments in the rendered scene. For example, in FIG. 2, ablation needle 242 can be held in the healthcare provider's left hand and the medical device shaft is to the left of the 3D ultrasound image slice, so that the 2D view 202 of the ultrasound image in the upper right corner of display 220 does not cover any of the 3D features of the medical device (or vice-versa). If the medical device were held in the healthcare provider's right hand, the virtual medical device shaft would appear on the right side. To prevent the 2D view 202 in the corner of display 220 from covering the medical device shaft, the system can automatically move it to a corner that would not otherwise be occupied by graphics or data.

In some embodiments, the system attempts to avoid having the 2D view 202 of the ultrasound image quickly moving among corners of the display in order to avoid overlapping with graphics and data in the display. For example, a function f can be used to determine which corner is most suitable for the 2D ultrasound image to be drawn in. The inputs to f can include the locations, in the screen coordinate system, of the displayed medical device tip, the corners of the 3D ultrasound image, etc. In some embodiments, f's output for any given point in time is independent of f's output in the previous frames, which can cause the ultrasound image to move among corners of the display rapidly. In some embodiments, the image guidance system will filter f's output over time. For example, the output of a filter g, for any given frame, could be the corner which has been output by f the most number of times over the last n frames, possibly weighting the most recent values for f most heavily. The output of the filter g can be used to determine in which corner of display 220 to display the 2D ultrasound image and the temporal filtering provided by g can allow the 2D view 205 of the ultrasound image display to move more smoothly among the corners of the display 220.

In some embodiments, other appropriate virtual information and/or image guidance cues can be overlaid on the 2D view 205 of the ultrasound image as well as the 3D view 204. Examples include: orientation indicator 214, an indication of the distance between the medical device's tip and the point in the plane of the ultrasound image that is closest to the medical device tip; the cross section or outline of the ablation volume that intersects with the ultrasound slice; and/or the intersection point, box, outline, etc. between the medical device's axis and the ultrasound image plane.

Furthermore, it will be understood that other image guidance cues can be generated and displayed on the display as described in greater detail in the '274 application, previously incorporated herein by reference. For example, the system 100 can generate and/or display graphical indicators that help indicate the spatial relationship between a medical device and an ultrasound image plane (e.g., graphical image plane indicators) or other plane (e.g., graphical plane indicators), indicators to indicate the relative positions of the medical device(s) and ultrasound image, features of interest, annotations, foundational plane indicators, foundational plane intersection indicators, other graphical indicators, approximate medical device location indicators, etc. As described in greater detail above and in the '274 application, the various image guidance cues can be generated based at least in part on the emplacement information of the medical devices used with the system 100.

Configuring the Point-of-View Location

Figure 3B:
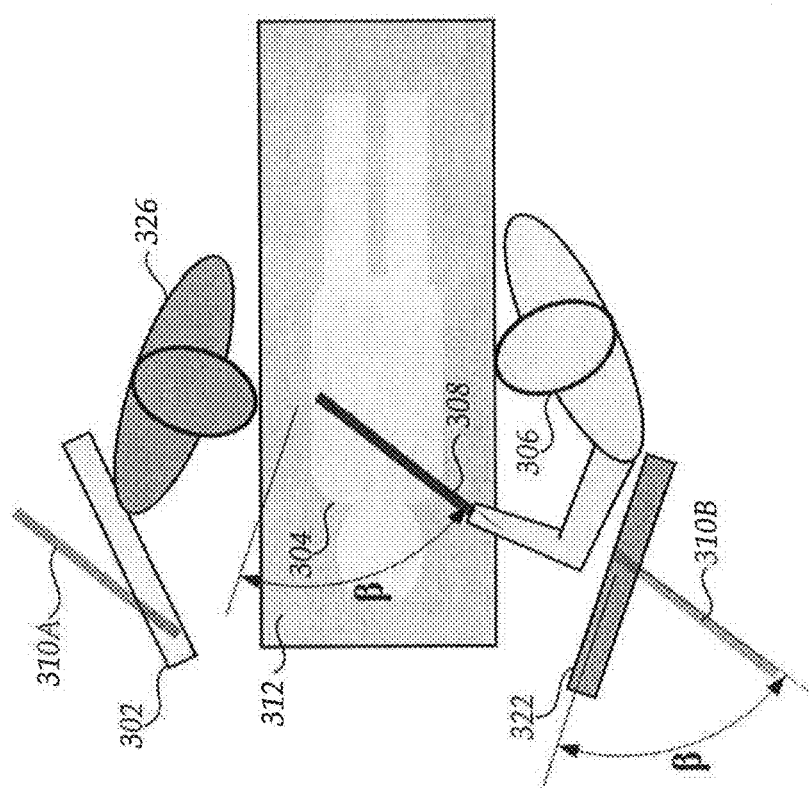
FIG. 3B is a diagram illustrating an embodiment with multiple displays displaying different perspective views of a virtual medical device based on the pose of the medical device with respect to different point-of-view locations.
Figure 3A:
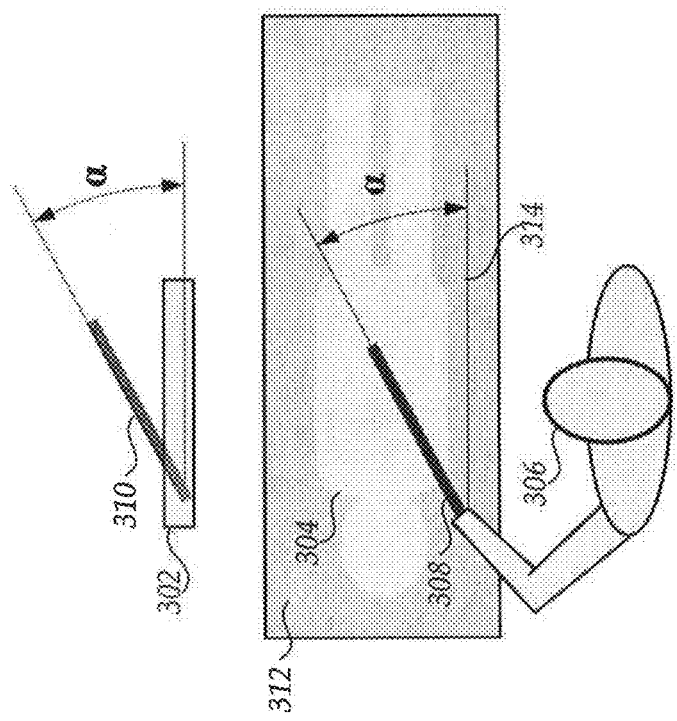
FIG. 3A is a diagram illustrating an embodiment of the relative location of a display with respect to a patient and a user.

FIG. 3A is a diagram illustrating an embodiment of the relative location of a display 302 with respect to a patient 304 and a user 306. In the illustrated embodiment, the display 302 is located on one side of the patient 304, and the user 306 is located on an opposite side. However, it will be understood that the display 302 and/or user 306 can be located in any configuration, as desired. In addition, in the illustrated embodiment, the user 306 is holding a medical device 308 at an angle alpha with respect to an axis of the display 302.

Although not illustrated in FIG. 3A, a pose sensor can be coupled with medical device 308. Based at least on the emplacement information received from the pose sensor, the system can determine the relative pose of the medical device 308 with respect to the point of view location (which is some distance in front of the display 302 in the illustrated embodiment) and display a perspective view of a virtual medical device 310 on the display based at least in part on the determined relative pose. Although the illustrated embodiment of FIG. 3A shows only the angle alpha, it will be understood that the medical device can be orientated at any angle with respect to the display and/or the point-of-view location.

In some embodiments, the user 306 can alter the point-of-view location of the system. For example, if the user moves the display 302 to the foot of the patient 304, the user may want to change the point-of-view location to coincide with the new relative pose between the user and the display. As another example the system may have a default point-of-view location that requires the position sensing unit to be orientated in a particular way with respect to the display and/or the user. As such, the user may want to alter the point-of-view location based on an actual pose of the position sensing unit with respect to the user and/or display.

To alter or configure the point-of-view location, the user 304 can position the medical device 308 at a predetermined pose with respect to the display 302. The predetermined pose can be pre-programmed into the system or dynamically selected by the user. For example, in some embodiments, the predetermined pose can be orthogonal or parallel to the display 302.

Once the medical device 308 is oriented in the predetermined pose, the user 306 can enter a command into the system. The user 306 can enter the command in a variety of ways, such as, but not limited to, pressing a button or pedal, clicking/moving a mouse, touching the display 302, gesturing with the body (hand, foot, head) or medical device, etc.

As part of the configuration process, the system 100 can determine the relative pose of the medical device with respect to a reference location. The reference location can refer to the location of the position sensing unit, such as a magnetic and/or optical tracker, or other type of position sensing device, the location of a portion of the position sensing unit, and/or a coordinate system of the position sensing unit. For example, if the position sensing unit is located on or below the table and orientated in the same way as the table, the reference location can be the coordinate system of the position sensing unit. For example, the reference location may have an x-axis along the length of the table 312, a y-axis along the width of the table 312, and a z-axis up and down from the table 312. In some embodiments, the reference location can be a direction, such as a geographic direction (e.g., North, etc.).

Using the relative pose of the medical device 308 with respect to the reference location, as well as the known relative pose of the predetermined pose with respect to the display, the system can determine the point-of-view location. For example, with reference to the illustrated embodiment of FIG. 3A, if the predetermined pose is parallel to the display 302, and the system determines that the medical device 308 is orientated along the line 314 when the command is entered, the system can determine that the position sensing unit is orientated such that the length of the position sensing unit (and table 312) is parallel to the screen 302 and the width of the position sensing unit is perpendicular to the screen 302. Furthermore, the system can determine that the point-of-view location is somewhere along the y-direction of the position sensing unit. In some embodiments, the exact location of the point-of-view location is estimated based at least in part on an expected distance of the display 302 from the table 312. In some embodiments, the system can determine the location of the medical device 308 with respect to the position sensing unit and use that location as the point-of-view location. In certain embodiments, the point-of-view location is one, both, or a combination of orientation and a location.

Once the point-of-view location is configured, the system can display perspective views of the virtual medical device 310 with respect to the point-of-view location. For example, as illustrated in FIG. 3A, the system can display the virtual medical device 310 at an angle alpha, which represents the angle difference between the medical device 308 and the point-of-view location.

FIG. 3B is a diagram illustrating an embodiment with multiple displays 302, 322 displaying different perspective views of the virtual medical device 310A, 310B based on the pose of the medical device 308 with respect to different point-of-view locations (or the different displays 302, 322) As described in greater detail above, with reference to FIG. 3A, the user 306 (or user 326) can configure the different point-of-view locations for the different displays 302, 322. For example, the user 306 can place the medical device 308 in a predetermined pose with respect to the display device 302 and then enter the configuration command. Using the known pose of the predetermined pose with respect to the display device 302 and the pose of the medical device 308 with respect to the position sensing unit, the system can determine the point-of-view location for the display device 302.

Similarly, the user 306 (or user 326) can configure the point-of-view location for the second display 322. For example, the user 326 can orient the medical device 308 in the predetermined pose with respect to the display device 322 and then enter the configuration command. Using the known pose of the predetermined pose with respect to the display device 322 and the pose of the medical device 308 with respect to the position sensing unit, the system can determine the point-of-view location for the display device 322. In this way, each user can see a perspective view of the virtual medical devices 310A, 310B from their respective points-of-view. For example, as illustrated, when the medical device 308 is orientated as shown in FIG. 3B, the virtual medical device 310A is shown pointing into the display 302 with the handle in the foreground with respect to the tip, while the virtual medical device 310B is shown pointing out of the display 322 with the handle in the background with respect to the tip. When the user 306 rotates the medical device 308 by angle beta and the medical device 308 is parallel (or approximately parallel) to the display 322, the virtual medical device 310B can appear to be parallel (or approximately parallel) to the display 322, while the virtual medical device 310A can appear angled with respect to the display 302 (e.g., the handle will be in the background with respect to the tip).

It will be understood that the system can perform any or all of the functions described herein and in the '274 application, for one or both of the displays 302, 322. In this way, the system can display different perspective views of the virtual medical device based at least in part on the pose of the medical device with respect to different point-of-view locations.

In some embodiments, the system 100 can automatically determine the point-of-view location(s) based at least in part on emplacement information of the medical device 308, the position sensing unit, and the one or more sets of one or more displays 302, 322. For example, in some embodiments, the medical device 308, the position sensing unit, and the display(s) 302, 322 can each include a tracking unit (e.g., pose sensor). The emplacement information of the medical device 308, the position sensing unit, and the display(s) 302, 322 can be communicated to the position sensing unit. Based on the emplacement information, the position sensing unit can determine the pose of the position sensing unit with respect to the display and/or the user(s), and also determine the point-of-view location(s). For example, in some embodiments, the system 100 can determine the point-of-view location to be in front of the display(s) 302, 322, regardless of the current pose of the medical device 308 and/or the position sensing unit with respect to the displays 302, 322.

It will be understood that the system can use additional point-of-view locations as desired. In addition, multiple perspective views of the virtual medical device can be displayed on a single display based on different point-of-view locations. Furthermore, in some embodiments, each point-of-view location includes a right eye/left eye point of view location.

FIG. 4 is a flow diagram illustrative of an embodiment of a routine 400 implemented by the system 100 to configure a point-of-view location. One skilled in the relevant art will appreciate that the elements outlined for routine 400 can be implemented by one or more computing devices/components that are associated with the system 100, such as the position sensing unit 140, the image guidance unit 130, surgical system 149, and/or imaging unit 150. Accordingly, routine 400 has been logically associated as being generally performed by the system 100. However, the following illustrative embodiment should not be construed as limiting.

At block 402, the system 100 receives a configuration command. The configuration command can be implemented in a variety of ways. For example, in some embodiments, the configuration command can be implemented as a button pressed by a user on the keyboard, a mouse click, touch of the display, hand gesture, head gesture, medical device gesture, or other gesture with the body, etc.

In some embodiments, prior to receiving the configuration command, the medical device can be orientated according to a predetermined pose. For example, a user can orient the medical device so that it is in the predetermined pose with respect to the display. The predetermined pose can be determined at manufacturing and/or dynamically selected by a user. For example, the predetermined pose can be orthogonal to the display and/or centered (horizontally and/or vertically) with the display. In some embodiments, the predetermined pose can be parallel to the display, etc.

At block 404, the system 100 determines the pose of a medical device with respect to a reference location based at least in part on received emplacement information of the medical device. As described previously, the emplacement information can be received from a tracking unit coupled and/or embedded with the medical device.

The reference location can refer to the location of the position sensing unit, such as a magnetic and/or optical tracker, or other type of position sensing device, the location of a portion of the position sensing unit, and/or a coordinate system of the position sensing unit. In some embodiments, the reference location can be a geographical direction, such as North, etc.

By determining the pose of the medical device with respect to the reference location, the system 100 can determine a pose relationship between the medical device and the reference location. In some embodiments, the system 100 can determine that the medical device is pointing towards the reference location, away from the reference location, is centered (or off to the right or left, in front of, behind) with respect to the reference location, is above/below the reference location, etc. For example, the system 100 can determine that the medical device is pointing North, is pointing at or away from the position sensing unit, is pointing at or away from a portion of the position sensing unit, is parallel or orthogonal to (or somewhere in between) the position sensing unit, is to the left or right, in front of or behind, above or below, the position sensing unit, etc.

In some embodiments, the system 100 can determine the pose of the medical device with respect to the coordinate system of the position sensing unit. For example, the system 100 can determine whether the medical device is parallel or orthogonal to an axis of the coordinate system, whether the medical device is centered on the coordinate system, near a minimum/maximum of the coordinate system, at the origin of the coordinate system, and/or can determine the angle of the medical device with respect to the axis of the coordinate system. For example, if the position sensing unit includes an electromagnetic field generator with the x-axis being the width of the field generator, the y-axis being the length of the field generator, and the z-axis being up/down, the position sensing unit can determine the relative pose of the medical device with respect to the x, y, and z axis of the field generator (position and/or orientation).

At block 406, the system 100 determines a point-of-view location based at least in part on the determined pose of the medical device with respect to the reference location. The point-of-view location can refer to the location from which a virtual 3D space is viewed and can be any location as desired. For example, if the display is considered a window into the virtual 3D space, the point-of-view location can be the location of the window with respect to the objects in the virtual 3D space. In some embodiments, the point-of-view location can be any location with respect to the display, the medical device, and/or the position sensing unit. In some embodiments, the point-of-view location is a fixed location, such as in front of the display, etc.

In some embodiments, using the determined pose of the medical device with respect to the reference location, as well as the predetermined pose, the system 100 can determine the point-of-view location. For example, if the predetermined pose is parallel to the display, and the medical device is oriented according to the predetermined pose and is also parallel to the x-axis of the position sensing unit and orthogonal to the y-axis of the position sensing unit, the system 100 can determine that the x-axis of the position sensing unit is parallel to the display. In addition, the system 100 can determine that the point-of-view location is located some distance away from the display in the y-direction of the position sensing unit's coordinate system. Accordingly, moving the medical device along the x-axis can cause the virtual medical device to move left or right, moving the medical device along the y-axis can cause the virtual medical device to move into or out of the display, and moving the medical device along the z-axis can cause the virtual medical device to move up or down.

Similarly, if the predetermined pose is orthogonal to the display, and the medical device is oriented according to the predetermined pose and is also parallel to the x-axis of the position sensing unit and orthogonal to the y-axis of the position sensing unit, the system 100 can determine that the y-axis of the position sensing unit is parallel to the display, and that the point-of-view location is located some distance away from the display in the x-direction of the position sensing unit's coordinate system.

In some embodiments, if the medical device is not orientated according to the predetermined pose when the point-of-view location is determined, the point-of-view location may be determined differently. For example, if the desired point-of-view location is somewhere along x-axis, but the medical device is orientated 90 degrees off from the predetermined pose, the system 100 can determine that the point-of-view location is somewhere along y-axis or z-axis, rather than the x-axis. Similarly, a different point-of-view location can be determined if the medical device is in a different location according to the predetermined pose when the point-of-view location is determined. For example, if the desired point-of-view location is directly in front of the display (e.g., centered with respect to the display), and the medical device is to the left or right of the display, the system 100 can determine that the point-of-view location is to the left or right of the center of the display. However, it will be understood that the predetermined pose can include one, both, or any combination of a predetermined orientation and a predetermined location.

At block 408, the system 100 determines a perspective view of a virtual medical device corresponding to the medical device based at least in part on the pose of the virtual medical device with respect to the point-of-view location. As described in greater detail above, the point-of-view location can be used to determine a perspective view of the virtual medical device. For example, the relative pose of the medical device with respect to the point-of-view location is used to determine the perspective view of the virtual medical device. Furthermore, as the pose of the medical device changes with respect to the point-of-view location, the perspective view of the virtual medical device can change as well.

At block 410, the system 100 causes one or more displays to display the perspective view of the virtual medical device in a virtual 3D space. As described in greater detail above and in the '274 application, perspective views of virtual medical devices can be displayed on one or more displays as desired.

It will be understood that fewer, more, or different blocks can be used as part of the routine 400. Furthermore, the order of the blocks can be changed as desired. For example, in some embodiments, the blocks 406 and 408 can be performed in parallel and/or the system 100 can omit block 402. In certain embodiments, the system 100 can determine a point-of-view location for each eye of a user. For example, the point-of-view location determined in block 406 can refer to a left eye or right eye (or centered between the two eyes) point-of-view location. The point-of-view location for the other eye (or each eye) can be determined by moving the determined point-of-view location by a predetermined amount (e.g., a few inches).

In certain embodiments, the system 100 can determine two point-of-view locations for two sets of one more displays. In some embodiments, the two sets of one or more displays may be offset by a certain number of degrees. For example, the two sets of one or more displays may be on opposite sides of a patient.

To determine, the second point-of-view location, the system 100 can receive a second configuration command, and then perform block 404 based at least in part on the pose of the medical device at a current time (e.g., at a second time that is after a first time when the system performs block 404 to determine the first point-of-view location). The system 100 can then perform block 406 to determine the second point-of-view location. During operation, the system 100 can use the two point-of-view locations to determine perspective views of the medical device(s) for the two sets of one or more displays as desired.

In some embodiments, the routine 400 can further include any one or any combination of the embodiments described in the '274 application and/or the embodiments described herein with reference to FIGS. 6A, 6B, 8A, and 8B. For example in some embodiments, the routine 400 can include any one or any combination of: calculating a perspective view in a virtual 3D space of the at least one image based at least in part on the emplacement information of the second medical device with respect to the point-of-view location, causing the one or more displays to display the perspective view of the at least one image in the virtual 3D space, calculating a perspective view in the virtual 3D space of a virtual first medical device corresponding to the first medical device based at least in part on the emplacement information of the first medical device with respect to the point-of-view location and/or calculating a perspective view in the virtual 3D space of a virtual second medical device corresponding to the second medical device based at least in part on the emplacement information of the second medical device with respect to the point-of-view location, and causing the display device to display a perspective view of the at least one of the virtual first medical device and the virtual second medical device in the virtual 3D space. Any combination of the aforementioned embodiments can be used as desired.

Co-Located Display Objects

Figure 5:
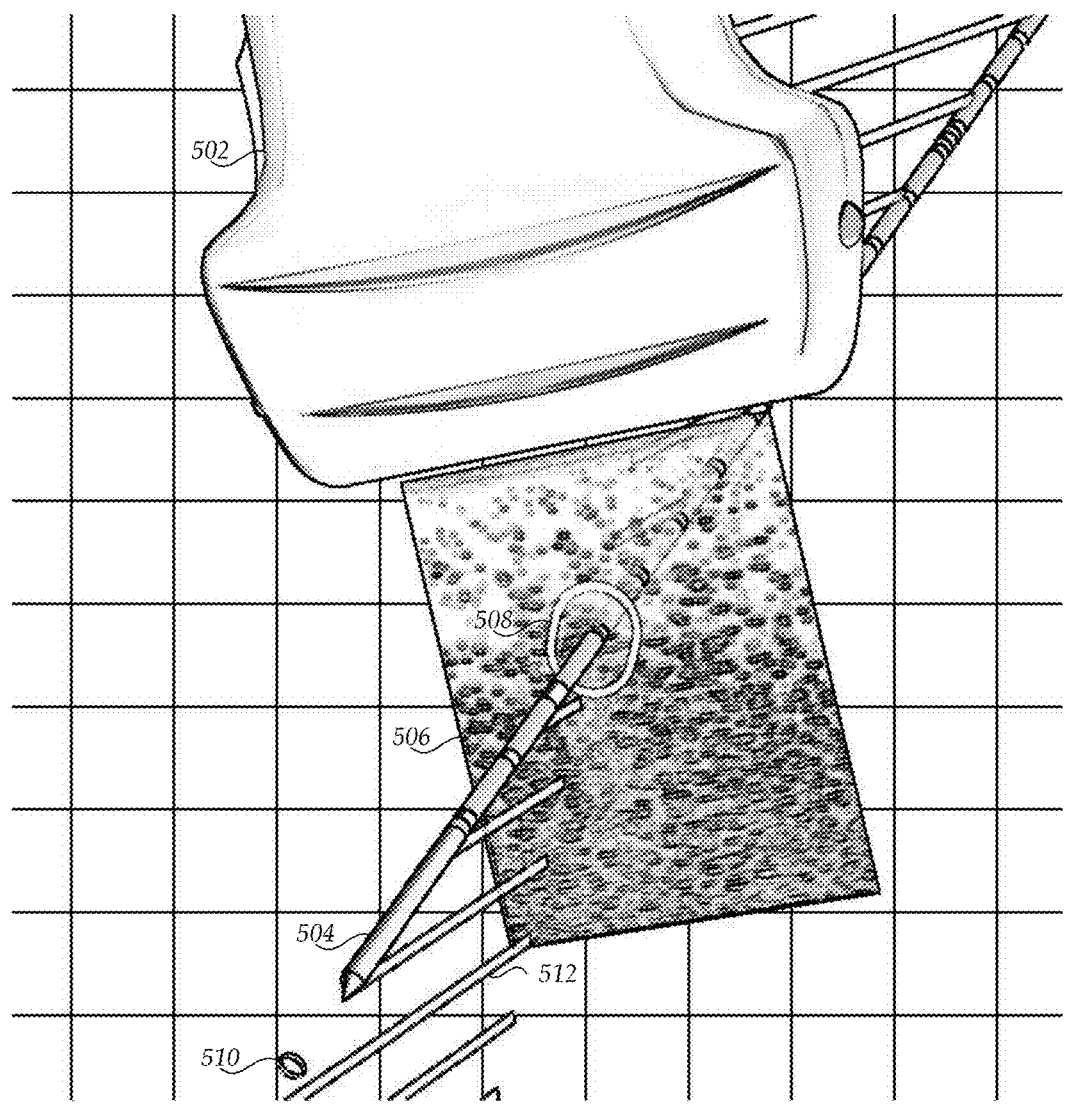
FIG. 5 is a diagram of an embodiment of rendered image guidance cues and medical display objects on a display.

FIG. 5 is a diagram of an embodiment of rendered display objects including image guidance cues and medical display objects on a display, such as the display 120. The diagram further includes gridlines indicating a background of a virtual 3D space in which the image guidance cues and medical display objects are located.

The medical display objects included in the illustrated embodiment can include a first virtual medical device 502, a second virtual medical device 504, and a rendered image 506. The image guidance cues included in the illustrated embodiment can include an intersection indicator 508, trajectory indicators 510 and graphical image plane indicators 512, each of which are described in greater detail above and/or in the '274 application.

As mentioned previously, in some cases, when two display objects are co-located on a display, the system 100 can change from displaying one display object to the other display object and back, repeatedly. This oscillation between the two objects can create a flicker or other distortion on the display. In some embodiments, to resolve this issue, the system 100 can display one display object in front of the other. In some embodiments, the system gives one of the objects priority. The object given priority (or the object with a higher priority) can then be displayed in front of the other object.

The system can give display objects priority in a number of ways. For example, the priority of some objects can be predetermined or can be dynamically determined by the user. For example, the system can have a listing of the priority levels of the different display objects. For example, in some embodiments, the medical display objects 502, 504, 506 can be given a lower priority level than the image guidance cues, or vice versa. Similarly, different medical device objects can be given a higher priority level than others. For example, the rendered image 506 can be given a lower priority level than the virtual medical devices 502, 504, or vice versa. Similarly, different image guidance cues 508, 510, 512 can be given higher priority levels than others. For example, the intersection indicator 508 can be given a higher priority level than the trajectory indicators 510 and/or the graphical plane indicators 512. Any combination of priority levels can be given to the different display objects as desired. Furthermore, the priority levels of the display objects can be changed as desired.

The system can cause the one or more displays to display one object (e.g., the object with the higher priority) in front of the other object in a variety of ways. For example, in some embodiments, the system can compare the priority levels and display the display object with the higher priority level in place of, or in front of, the other display object. In some embodiments, the display object displayed in front of the other can be transparent or translucent such that the display object on bottom (or behind) can still be seen.

In certain embodiments, the system can alter the location or coordinates of a display object in order to cause the one or more displays to display one object in front of the other. In some embodiments, the system can alter the location of the display object with the higher or lower priority such that it is no longer co-located with the other object. For example, if a portion of an image guidance cue is co-located with and has a higher priority than a portion of a medical display object, the system can move the portion of the image guidance cue forward with respect to the point-of-view location so that the portion of the image guidance cue is in front of the portion of the medical display object. Similarly, the system can move the medical display object backwards or move both the image guidance cue and the medical display object. It will be understood that the system can move the display objects in any direction and combination as desired. Once one or both display objects are moved, the system can render the display object as it normally would. The system can perform a similar process for three or more co-located display objects.

In some instances, to move the display object, the system can alter the coordinates of the portion of the display object. In some embodiments, the system can alter one or more bits or registers that indicate the location of the image guidance cue. In certain embodiments, the system moves the display object so that the movement is imperceptible to a user. For example, a user may not be able to discern if the display object is moved by a millimeter, a pixel, one or more bits, etc. In some embodiments, the system moves the display object by one or more bits. In certain embodiments, the system moves the display object by the smallest allowable increment (e.g., one or more bits, pixels, etc.).

As an example, and not to be construed as limiting, in the illustrated embodiment of FIG. 5, the intersection indicator 508 can be co-located with at least a portion of the rendered image 506. As such, the system may oscillate between displaying the portions of the intersection indicator 508 and portions of the rendered image 506. In some embodiments, to resolve this issue, the system can compare the priority levels of the intersection indicator 508 and the rendered image 506 to determine which display object should be displayed in front of the other. In certain embodiments, the system can determine that when the intersection indicator 508 and the rendered image 506 are co-located, the intersection indicator 508 is to be displayed in front of the rendered image 506. Based on the determination, the system can display the intersection indicator 508 in front of the rendered image 506. In some embodiments, the system can move the intersection indicator 508 and/or the rendered image 506 so that the system considers the intersection indicator 508 in front of the rendered image 506. Once moved, the system can display the intersection indicator 508 in front of the rendered image 506.

Figure 6A:
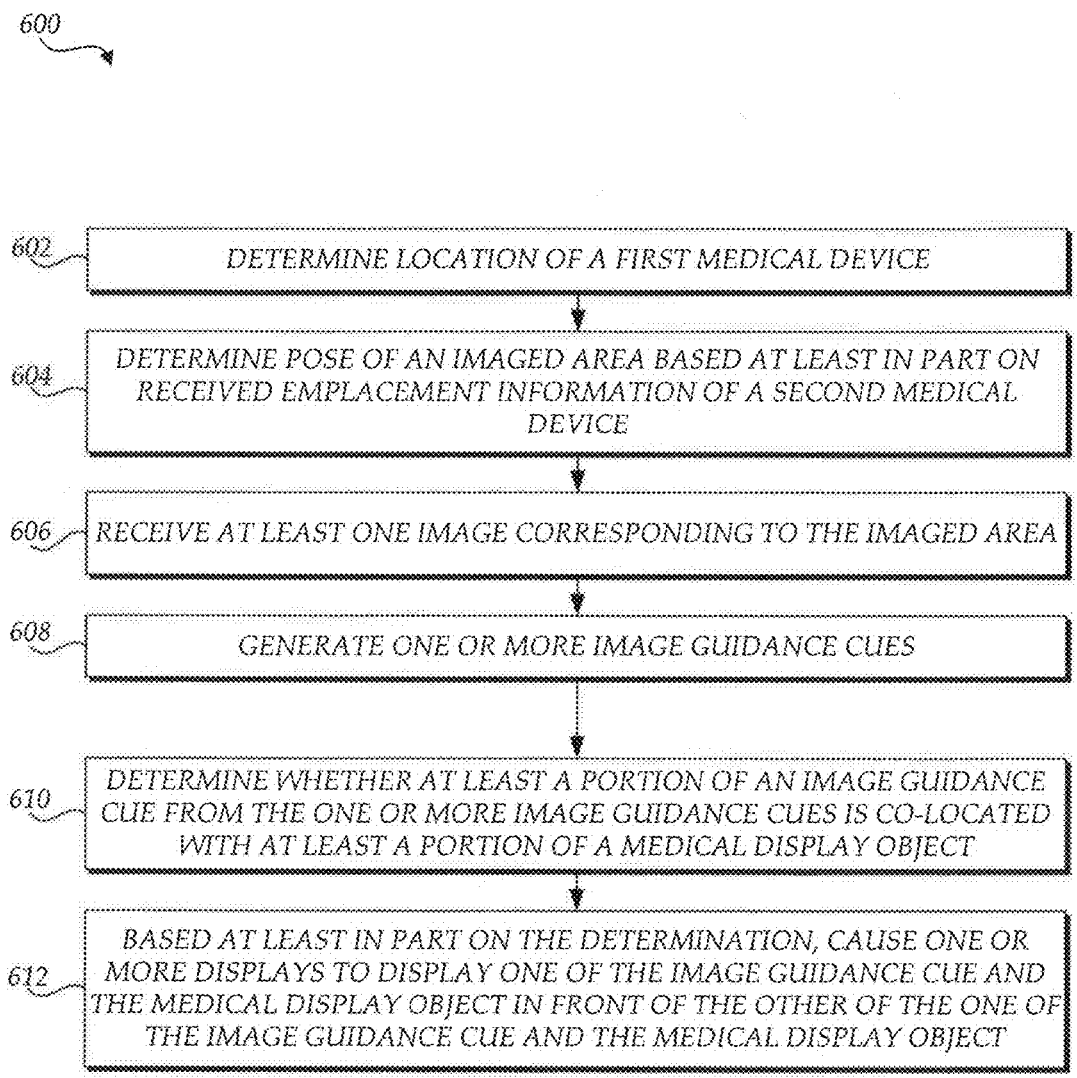
FIG. 6A is a flow diagram illustrative of another embodiment of a routine implemented by the system to resolve co-located display objects.

FIG. 6A is a flow diagram illustrative of an embodiment of a routine 600 implemented by the system 100 to resolve co-located display objects. One skilled in the relevant art will appreciate that the elements outlined for routine 600 can be implemented by one or more computing devices/components that are associated with the system 100, such as the position sensing unit 140, the image guidance unit 130, surgical system 149, and/or imaging unit 150. Accordingly, routine 600 has been logically associated as being generally performed by the system 100. However, the following illustrative embodiment should not be construed as limiting.

At block 602, the system 100 determines pose of a first medical device based at least in part on emplacement information of the first medical device. In certain embodiments, the system 100 receives emplacement information of one or more medical devices within a predetermined area and uses that information to determine the pose of the one or more medical devices. In some embodiments, the medical devices are invasive medical devices, such as ablation or biopsy needles, catheters, etc. As described previously, the medical devices, such as needles, can include tips, electrodes, and handles. In certain embodiments, the medical devices are non-invasive medical devices. In some embodiments, the medical devices are medical imaging devices, such as ultrasound transducers and/or laparoscopic cameras.

As described in greater detail above with reference to FIG. 1, each medical device can be associated with a tracking unit that provides emplacement information, such as pose information. As described previously, the tracking units can be coupled with and/or implanted into the medical devices. Using the emplacement information of the tracking unit and known characteristics of the first medical device, the pose for the first medical device can be determined. Accordingly, by receiving emplacement information from a tracking unit, the system 100 can also receive and/or determine the pose of the first medical device.

At block 604, the system 100 determines the pose of an imaged area based at least in part on received emplacement information of a second medical device. As mentioned previously, the system 100 can receive emplacement information for any number of medical devices and use that information to determine the pose of the respective medical devices.

In addition, in some embodiments, the system can use the received emplacement information to determine the pose of an imaged area that is associated with and/or corresponds to a medical device. For example, the second medical imaging device can be an ultrasound transducer and can generate ultrasound images. Based on the known characteristics of the ultrasound transducer, such as the dimensions of its corresponding ultrasound slice (e.g., width and depth of ultrasound slice, shape of ultrasound slice, etc.), the system 100 can determine the pose of the imaged area (e.g., the area that is captured by the ultrasound transducer and/or covered by the ultrasound slice).

As described in greater detail above with reference to FIG. 1, in some embodiments, the second medical device can be used to select image data from a set of image data stored previously. The dimensions of the selected image data (or imaged area) can be selected by the user and/or determined at manufacturing. For example, the area of the selected image data can be the area that is covered by the last two inches of a distal portion of the second medical device and six inches below the second medical device. Based on the known dimensions and location of the imaged area with respect to the second medical device, the system 100 can determine the pose of the imaged area based at least in part on the emplacement information of the second medical device.

At block 606, the system 100 receives image data based at least on the emplacement information of the second medical device. In some embodiments, the system 100 receives one or more images from the second medical device. For example, the second medical device can be a medical imaging device, such as an ultrasound transducer and can provide one or more ultrasound images to the system 100. As described in greater detail above with reference to FIG. 1, in some embodiments, the second medical device is used to select image data from a set of image data stored previously. For example, based on the emplacement of the second medical device, the system can receive images corresponding to a CT scan or MRI. In such embodiments, any device can be used as the second medical device.

At block 608, the system generates one or more image guidance cues. The image guidance cues can include, but are not limited to, trajectory indicators (e.g., medical device and/or needle drive indicators), intersection indicators (e.g., image plane intersection indicators, foundational plane intersection indicators, etc.), ablation zone indicators, spatial indicators (e.g., relative spatial indicators), graphical indicators (e.g., graphical plane indicators), foundational plane indicators, approximate medical device location indicators, etc. As described in greater detail above and in the '274 application, the various image guidance cues can be generated based at least in part on the emplacement information of the medical devices used with the system 100.

At block 610, the system determines whether at least a portion of an image guidance cue from the one or more image guidance cues is co-located with at least a portion of a medical display object. The medical display object can include, but is not limited to, a first virtual medical device corresponding to the first virtual medical device, a second virtual medical device corresponding to the second medical device medical device, the image, the rendered image, the rendered image area, and/or one or more additional medical devices.

In some embodiments, to determine whether the portion of the image guidance cue and the portion of the medical display object are co-located, the system 100 can compare the coordinates of the portion of the image guidance cue with the portion of the medical display object. If the coordinates (e.g., the x, y, z coordinates) match (e.g., are equal) or satisfy a distance threshold, the system can determine that the portion of the medical display object and the portion of the image guidance cue are co-located. In certain embodiments, the system 100 can determine that the portion of the image guidance cue and the portion of the medical display object are co-located if the portion of the image guidance cue and the portion of the medical display object can be mapped to the same pixel in a video or image output data buffer.

The distance threshold can be a predefined distance, such as one or more bits, one or more pixels, etc. In some embodiments, the distance threshold can be based at least in part on whether the distance between the coordinates is perceptible to a user, which may be based at least in part on the size of the display, the size of the display relative to the image and/or imaged area, and/or the distance between the point-of-view location and the display, etc. For example, in some case the distance threshold can be smaller for larger displays (or larger display:image ratios) and larger for smaller displays (or smaller display:image ratios), or vice versa. In certain cases, the distance threshold can be larger for larger distances between the point-of-view location and the display and smaller for smaller distances between the point-of-view location and the display, or vice versa. In certain embodiments, the distance threshold can be different for each coordinate.

In certain embodiments, the system 100 can perform the comparison for each location of the medical display objects and/or each location of the image guidance cues. In some cases, the system can determine that the portion of the medical display object and the portion of the image guidance cue are co-located if the portion of the medical display object and the portion of the image guidance cue are co-located are level and have the same depth.

In some embodiments, for each location on the display, the system can query whether a portion of the medical display object and/or a portion of the image guidance cue have been (or will be) mapped to that location. If the system 100 determines that a portion of the medical display object and a portion of the image guidance cue have been (or will be) mapped to that location, the system 100 can determine that the portion of the medical display object and the portion of the image guidance cue are co-located.

At block 612, the system 100 causes the one or more displays to display one of the portion of the image guidance cue and the portion of the display object in front of the other of the one of the portion of the image guidance cue and the portion of the medical display object. In some embodiments, the system 100 does this based at least in part on a determination that the portion of the image guidance cue is co-located with the portion of the medical display object.

To cause the one or more displays to display the portion of the image guidance cue or the portion of the display object in front of the other, the system 100 can overlay one portion on top of the other. In some embodiments, the system 100 overlays one portion on top of the other such that the portion on bottom cannot be seen (e.g., the portion on top is opaque). In certain embodiments, the system 100 causes the one or more displays to display the portion on top semi-transparently or more transparently than the portion on bottom (e.g., at a transparency level that is greater than the transparency level of the portion on bottom, etc.).

In certain embodiments, to cause the one or more displays to display the portion of the image guidance cue or the portion of the display object in front of the other, the system 100 can move one of the portions with respect to the other. In some embodiments, the system 100 can move the portion of the image guidance cue so that it is no longer co-located with the portion of the medical display object, or vice versa. For example, the system 100 can alter the depth (e.g., z coordinate with reference to the display coordinate system) of the portion of the image guidance cue so that it is in front of or behind the portion of the medical display object, or vice versa. However, it will be understood that the system 100 can alter any coordinate of the portion of the image guidance cue and/or the portion of the medical display object.

Furthermore, the system 100 can move the portion by any amount as desired. In some embodiments, the system 100 can move the portion by a relatively small increment, such as, for example, by one or more bits (the bits representing the depth, or other coordinate, of the portion). In certain embodiments, the system 100 moves the portion by the smallest available increment. For example, the system can move the portion by a single bit. By moving the one portion relative to the other portion, the system 100 can more easily determine how to display the different portions. For example, the system 100 can determine that one portion is in front of the other portion.

It will be understood that the order of the blocks can be changed as desired. For example, in some embodiments, the blocks 602 and 604 can be performed in parallel. In addition, the system 100 can perform similar routines for any number of display objects (e.g., one or image guidance cues and/or one or more medical display objects) as desired.

Furthermore, it will be understood that fewer, more, or different blocks can be used as part of the routine 600. For example, in some embodiments, the system 100 can omit block 606. In certain embodiments, the system 100 can cause the one or more displays to display the image guidance cues, determine and cause the one or more displays to display perspective views of the medical display objects. As part of determining the perspective views, the system 100, in some embodiments, can determine and cause to be displayed a perspective view of the portion of the image guidance cue and/or the portion of the first medical device object, as desired.

Figure 6B:
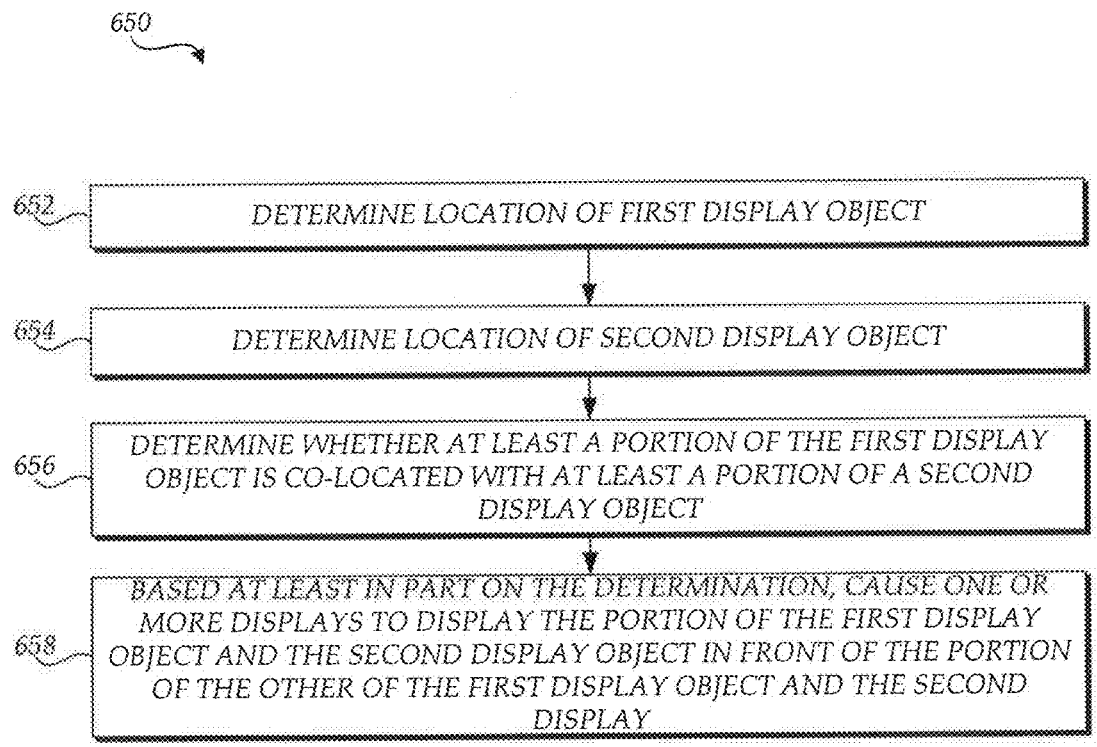
FIG. 6B is a flow diagram illustrative of an embodiment of a routine implemented by the system to resolve co-located display objects.

FIG. 6B is a flow diagram illustrative of an embodiment of a routine 650 implemented by the system 100 to resolve co-located display objects. One skilled in the relevant art will appreciate that the elements outlined for routine 650 can be implemented by one or more computing devices/components that are associated with the system 100, such as the position sensing unit 140, the image guidance unit 40, surgical system 149, and/or imaging unit 150. Accordingly, routine 650 has been logically associated as being generally performed by the system 100. However, the following illustrative embodiment should not be construed as limiting.

At block 652, the system 100 determines a location of a first display object. As mentioned previously, the display object can include, but is not limited to medical display objects (e.g., virtual medical device, rendered image, etc.) and/or image guidance cues (trajectory indicators, intersection indicators, graphical plane indicators, etc.). To determine the location of the first display object, the system can determine where the display object is, or would be, located on a display. For example, the system 100 can refer to a video or image output buffer to determine the location of the first display object. Furthermore, the location can include one or more 2D or 3D coordinates as desired. For example, the first display object can have a volume associated with it based on the 2D or 3D coordinates. In some embodiments, the location of the display object is based at least in part on the pose of a physical medical device.

At block 654, the system 100 can determine a location of a second display object. The second display object can be a display object that is different from the first display object. For example, if the first display object is a virtual medical device and/or a graphical plane indicator, the second display object can be a rendered image, etc.). The location of the second display object can be determined in the same way as the location of the first display object.

At block 656, the system can determine whether at least a portion of the first display object is co-located with at least a portion of the second display object. In some embodiments, to determine whether the portion of the first display object is co-located with the portion of the second display object, the system 100 can compare the coordinates of the portion of the first display object with the coordinates of the portion of the second display object (e.g., in the video or image output buffer). If the coordinates (e.g., the x, y, z coordinates) match (e.g., are equal) or satisfy a distance threshold, the system can determine that the portion of the first display object is co-located with the portion of the second display object.

In certain embodiments, the system 100 can perform the comparison for each location of the medical display objects and/or each location of the image guidance cues. In some cases, the system can determine that the portion of the first display object is co-located with the portion of the second display object if the portion of the first display object is level with and has the same depth as the portion of the second display object. In some embodiments, for each location on the display, the system can query whether a portion of the first display object and/or a portion of the second display object have been mapped to that location. If the system 100 determines that a portion of the first display object and a portion of the second display object have been mapped to that location, the system 100 can determine that the portion of the medical display object and the portion of the image guidance cue are co-located.

At block 658, the system 100 causes the one or more displays to display one of the portion of the first display object and the portion of the second display object in front of the other of the one of the portion of the first display object and the portion of the second display object. In some embodiments, the system 100 does this based at least in part on a determination that the portion of the first display object is co-located with the portion of the second display object. In certain embodiments, the system 100 can determine which display object is to be displayed in front of the other based at least on a priority level of each object. For example, the display object with the higher priority can be displayed in front of the other. In certain embodiments, the system causes the one or more displays to display one of the display objects in front of the other by moving the display object.

It will be understood that fewer, more, or different blocks can be used as part of the routine 650. For example, in certain embodiments, the system 100 can determine and cause the one or more displays to display perspective views of display objects.

Figure 8A:
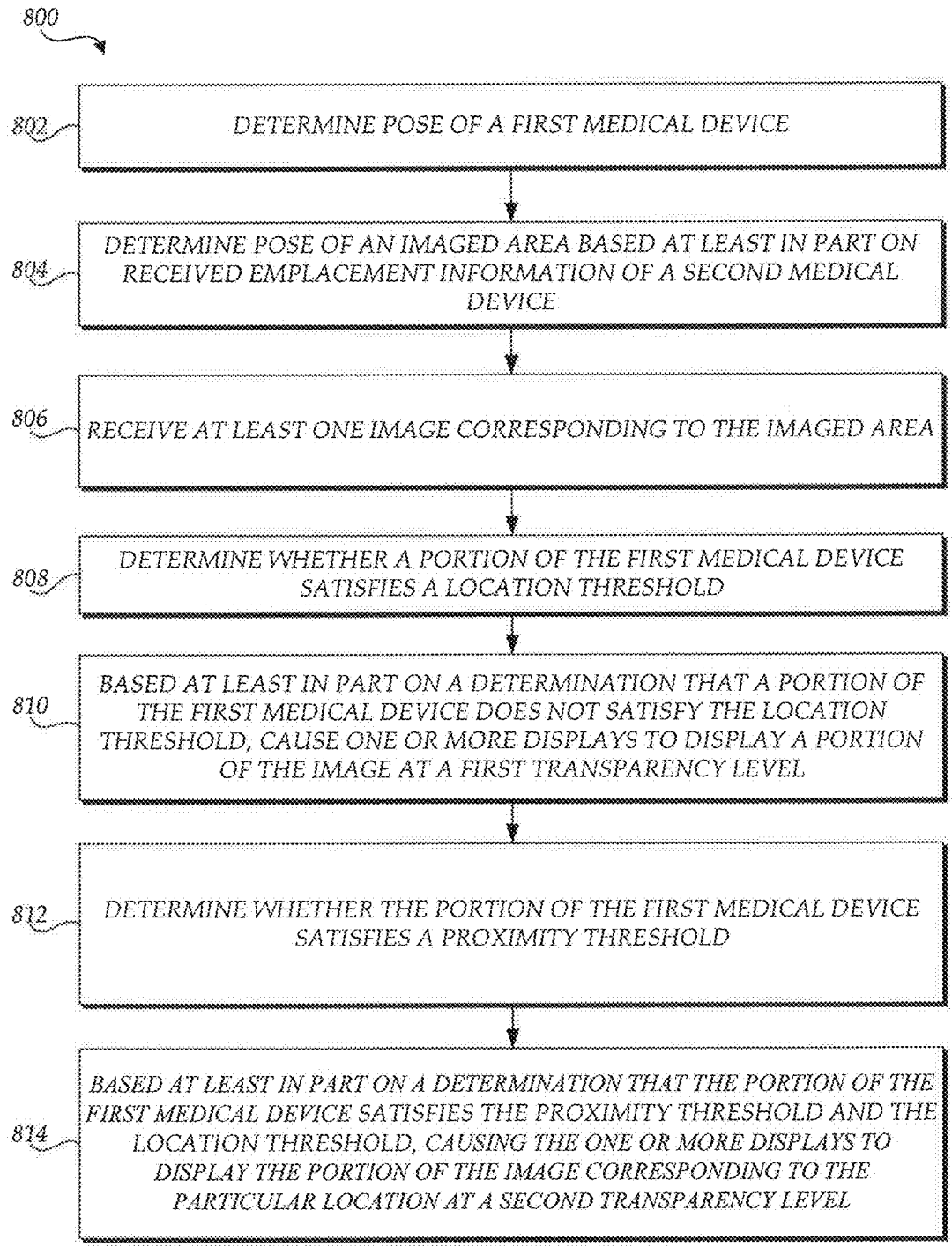
FIG. 8A is a flow diagram illustrative of an embodiment of a routine implemented by the system to display portions of a display object at different transparency levels.
Figure 8B:
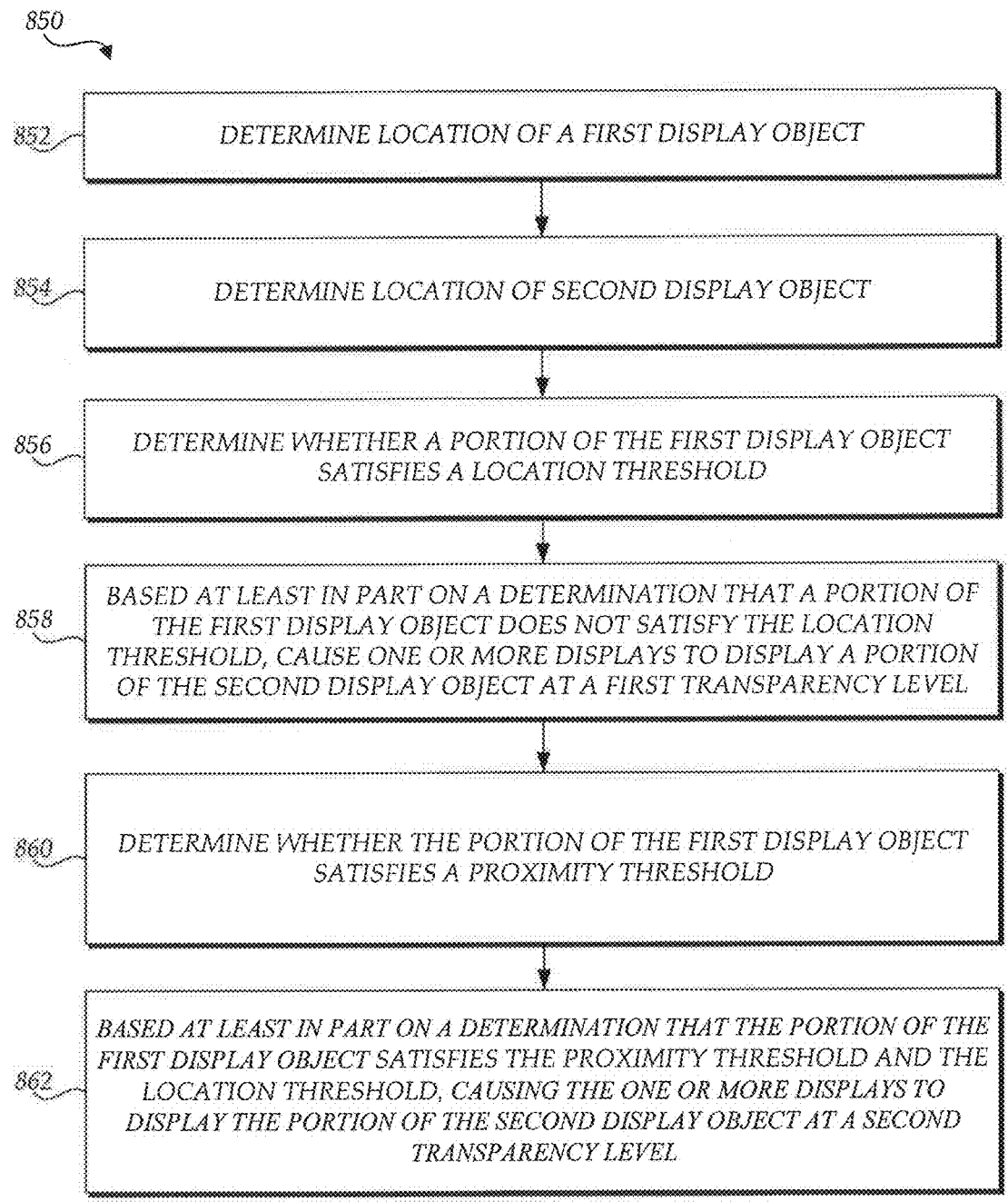
FIG. 8B is a flow diagram illustrative of another embodiment of a routine implemented by the system to display portions of a display object at different transparency levels.

In some embodiments, the routines 600, 650 can further include any one or any combination of the embodiments described in the '274 application and/or the embodiments described herein with references to FIGS. 4, 8A, and 8B. For example in some embodiments, the routines 600, 650 can include any one or any combination of: calculating a perspective view in a virtual 3D space of the at least one image based at least in part on the emplacement information of the second medical device with respect to the point-of-view location, causing the one or more displays to display the perspective view of the at least one image in the virtual 3D space, calculating a perspective view in the virtual 3D space of a virtual first medical device corresponding to the first medical device based at least in part on the emplacement information of the first medical device with respect to the point-of-view location and/or calculating a perspective view in the virtual 3D space of a virtual second medical device corresponding to the second medical device based at least in part on the emplacement information of the second medical device with respect to the point-of-view location, and causing the display device to display a perspective view of the at least one of the virtual first medical device and the virtual second medical device in the virtual 3D space. Any combination of the aforementioned embodiments can be used as desired.

Transparency Levels

With returned reference to FIG. 5, FIG. 5 also illustrates using different transparency levels for a display object. Specifically, FIG. 5 illustrates using different transparency levels for different portions of the rendered image 506.

As mentioned previously, in some systems, some display objects are displayed with a high transparency setting so that display objects behind it can be seen. For example, in order to see the medical device 504 when it is behind the rendered image 506, some systems would make the rendered image 506 transparent or translucent (or have a high transparency level). In such systems, the gridlines representing the background would be visible. However, by using a high transparency level, image intensity and contrast can be lost. As such by using a high transparency level for the entire rendered image 506, some features (e.g., tumors, body tissue, blood vessels, etc.) in the rendered image 506 may not be detected.

To alleviate this issue, the system can render those parts of the rendered image 506 (or other display object) that do not have another display object in front of or behind it at a low transparency level (e.g., opaque). For those parts of the rendered image 506 (or other display object) that have another display object behind it, the system can use a higher transparency level (more transparent). And for those parts of the rendered image 506 (or other display object) that have a display object in front of it, the system can render the other display object. As such, in some embodiments, the gridlines are not visible through any part of the rendered image 506 (or other display object).

The system can render the different portions of the rendered image 506 (or other display object) in a variety of ways. In some embodiments, the system determines for a particular location whether there is a portion of the rendered image 506 there and whether there is a portion of another display object behind the rendered image 506 (e.g., from the perspective of the point-of-view location). If the system determines that there is, the system can display the portion of the rendered image 506 at that particular location at a first transparency level, and in some embodiments, can also display the other display object. If the system determines that there is a portion of the rendered image 506 at the particular location and that there is not a portion of another display object at the particular location, the system can display the portion of the rendered image at that particular location at a second transparency level that is lower than (e.g., more opaque) the first transparency level.

For example, with reference to FIG. 5, the virtual medical device 504 is located in front of (e.g., from the perspective of the point-of-view location) the rendered image 506 from its tip to the intersection indicator 508. Similarly, the graphical image plane indicators 512 that are located to the left and below the intersection indicator 508 are in front of the rendered image 506. From the intersection indicator 508 to the top right corner of the rendered image 506, the virtual medical device 504 and corresponding graphical plane indicators 512 are located behind the rendered image 506.

Accordingly, for those locations on the rendered image 506 where the portions of other display objects (e.g., the medical device 504 and the graphical image plane indicators 512) are located in front of the rendered image 506 (e.g., portions the bottom left quadrant of the rendered image 506), the system can cause the one or more displays to display the portions of the other display objects (and, in some cases, not display the rendered image 506). For those locations on the rendered image 506 where the portions of the other display objects are located behind the rendered image 506 (e.g., the medical device 504 and the graphical image plane indicators 512 in the upper right quadrant of the rendered image 506), the system can cause the one or more displays to display the portions of the rendered image 506 at a first transparency level overlaid in front of (or on top of) the portions of the other display objects. Finally, for those locations on the rendered image 506 where there are no other display objects (e.g., bottom right quadrant of the rendered image 506, etc.), the system can cause the one or more displays to display the portions of the rendered image 506 at a second transparency level that is more opaque than the first transparency level.

Figure 7:
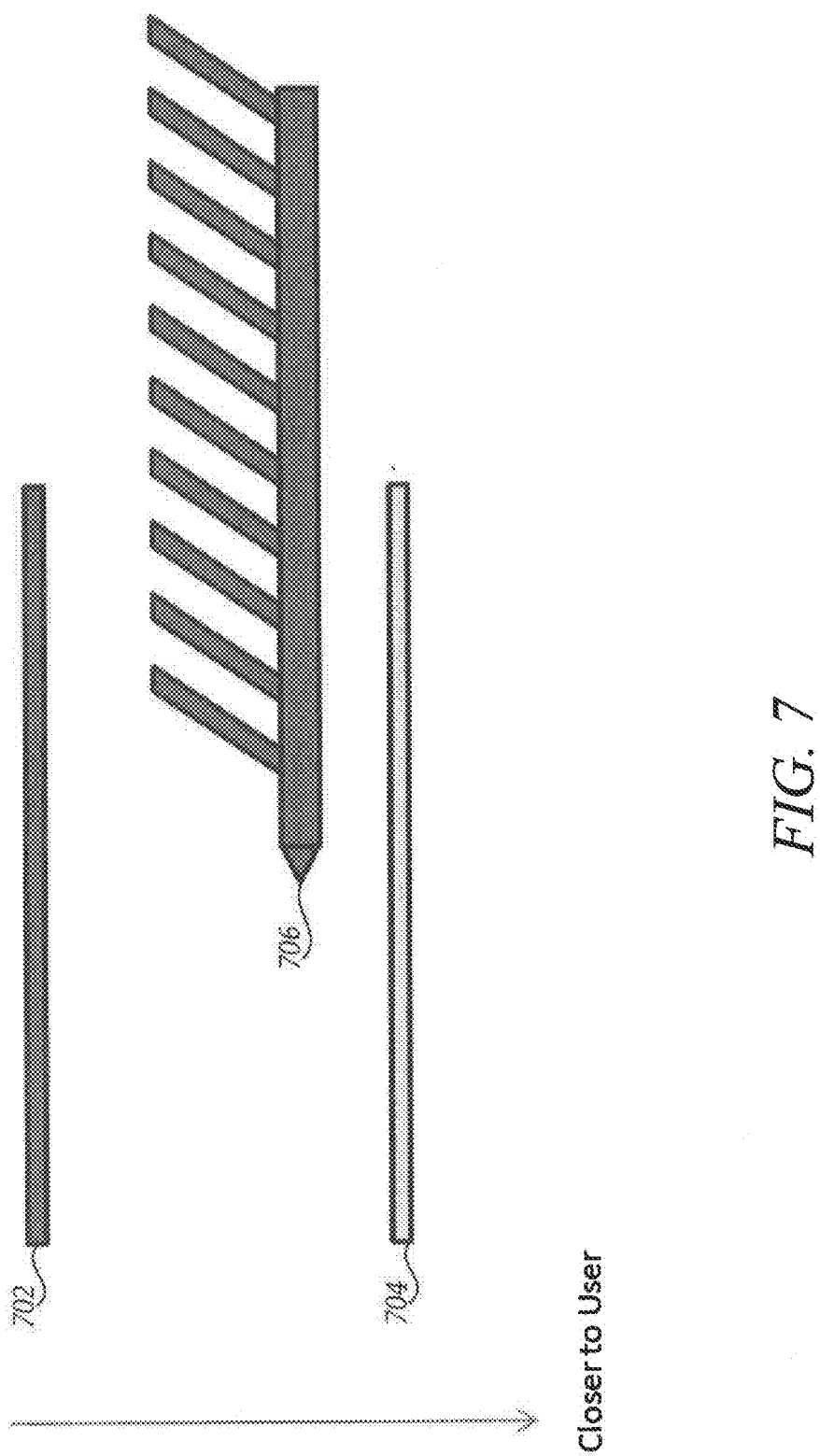
FIG. 7 is a diagram illustrative of an embodiment of two copies of an image and a virtual medical device.

With reference to FIG. 7, in some embodiments, the system can cause the one or more displays to display the portions of the rendered image at different transparency levels by using multiple copies of the rendered image. The first copy of the rendered image 702 can have a first transparency level (e.g., low transparency level and/or opaque) and the second copy 704 can have a second transparency level that is higher than the first transparency level.

In some embodiments, the system can cause the one or more displays to display the first copy of the rendered image 702. In certain embodiments, causing the one or more displays to display the first copy 702, can result in the gridlines illustrated in FIG. 5 to not be visible in the locations where the first copy 702 is displayed. The system can then, in some cases, cause the one or more displays to display in front of (or on top of) the first copy of the rendered image 702, the other display objects (e.g., virtual medical devices, image guidance cues, etc.) 706 that are to be located behind the rendered image on the display (e.g., from the perspective of the point-of-view location).

Once the other display objects 706 that are to be located behind the rendered image are placed in front of (or on top of) the first copy of the rendered image 702, the system can cause the one or more displays to display the second copy of the rendered image 704 in front of (or on top of) the first copy of the rendered image 702 and in front of (or on top of) the display objects 706 located behind the rendered image. The second copy 704 can have a second transparency level that is higher than the first transparency level (e.g., more transparent). As such, the second copy 704 can be overlaid in front of (or on top of) the display objects 706 that are to be located behind the rendered image. In some embodiments, the second copy 704 is sufficiently transparent such that the gridlines illustrated in FIG. 5 would be visible if the second copy 704 was displayed alone.

In addition, in some embodiments, the system can cause the one or more displays to display the display objects that are to be located in front of the rendered image in front of (or on top of) the first and second copies of the rendered image 702, 704. In this manner, the portions of the rendered image that do not have another display object in front of or behind it can be displayed more opaquely than the portions of the rendered image that have one or more display objects 706 behind them.

FIG. 8A is a flow diagram illustrative of an embodiment of a routine 800 implemented by the system 100 to display portions of a display object at different transparency levels. One skilled in the relevant art will appreciate that the elements outlined for routine 800 can be implemented by one or more computing devices/components that are associated with the system 100, such as the position sensing unit 140, the image guidance unit 130, surgical system 149, and/or imaging unit 150. Accordingly, routine 800 has been logically associated as being generally performed by the system 100. However, the following illustrative embodiment should not be construed as limiting.

At block 802, the system 100 determines pose of a first medical device based at least in part on emplacement information of the first medical device, as described in greater detail above with reference to block 602 of FIG. 6. At block 804, the system 100 determines a pose of an imaged area based at least in part on received emplacement information of a second medical device, as described in greater detail above with reference to block 605 of FIG. 6.

At block 806, the system 100 receives image data based at least on the emplacement information of the second medical device, as described in greater detail above with reference to block 606 of FIG. 6.

At block 808, the system 100 determines whether at least a portion of the first medical device satisfies a location threshold. In some embodiments, at block 808, the system 100 determines that at least a portion of the first medical device satisfies the location threshold. To determine whether a portion of the first medical device satisfies a location threshold, the system 100 can compare the coordinates of the first medical device with the coordinates of a particular location within the imaged area. The particular location can refer to a variety of locations within the imaged area and/or the imaged area as a whole. In some embodiments, the particular location can refer to a pixel that corresponds to the imaged area (e.g., a pixel within the imaged area). In certain embodiments, the pixel can correspond to a pixel on a display that displays an image of the imaged area, etc. In some embodiments, the particular location can refer to multiple pixels, such as an array of pixels, or other area within the imaged area, as desired.

Any coordinate system can be used to compare the coordinates of the portion of the first medical device with the particular location and/or to determine whether the portion of the first medical device is level with the particular location. For example, the coordinate system of the display and/or the coordinate system of device in the system 100 that is used to determine the pose of the medical devices can be used, as desired.

In some embodiments, the coordinate system of the display is used. The coordinate system of the display can be any pose as desired. In certain embodiments, the coordinates of the display are that the x-axis is the width of the display, the y-axis is the height of the display, and the z-axis is the depth (e.g., into and out of) the display. In such embodiments, the system 100 can determine that the portion of the first medical device satisfies the location threshold and/or is level with the particular location, based at least in part on the x and y coordinates of the first medical device and the x and y coordinates of the particular location. For example, if the x and y coordinates of the first medical device and the x and y coordinates of the particular location match (or satisfy a distance threshold), the system 100 can determine that the portion of the first medical device satisfies the location threshold.

Although reference is made to the x and y coordinates, it will be understood that the coordinates used to determine whether the portion of the first medical device satisfies the location threshold and/or is level with the particular location can be based at least in part on the coordinate system used. For example, in some embodiments, the coordinate system used can include the x-axis as the depth (e.g., forward/backward), the y-axis as lateral movement (e.g., side-to-side), and the z-axis as elevation (e.g., up/down). In such embodiments, the system 100 can determine that portion of the first medical device satisfies the location threshold if the y and z coordinates of the first medical device match (or satisfy a distance threshold) the y and z coordinates of the particular location.

In certain embodiments, the system 100 can determine that the portion of the first medical device satisfies the location threshold and/or is level with the particular location if the portion of the first medical device and the particular location (or portion of the image corresponding to the particular location) are co-located when mapped to a 2D plane. In some embodiments, the 2D plane can be based at least in part on the point-of-view location. For example, the 2D plane can be orthogonal to the point-of-view location. In certain embodiments, the system 100 can determine that the portion of the first medical device satisfies the location threshold (or corresponding virtual first medical device) if the portion of the first medical device overlaps with the particular location (or portion of the image corresponding to the particular location) in a virtual image (e.g., one is directly in front of or behind the other in the virtual image). In certain embodiments, the system 100 can determine that the portion of the first medical device satisfies the location threshold if the portion of the first medical device and the particular location (or portion of the image corresponding to the particular location) map to the same location on a display, such as the same pixel or same array of pixels.

At block 810, based at least in part on a determination that the portion of the of the first medical device does not satisfy the location threshold, the system 100 can cause the one or more displays to display a portion of the image corresponding to a particular location at a first transparency level. In some embodiments, the system 100 determines that the portion of the first medical device does not satisfy the location threshold and/or the portion of the first medical device is not level with the particular location based at least in part on a determination that the x and y coordinates (or other coordinates depending on coordinate system used) of the portion of the first medical device do not match (or do not satisfy the distance threshold) the x and y coordinates of the particular location mapped to the display (or portion of the image corresponding to the particular location). Similarly, the system 100 can determine that the portion of the first medical device does not satisfy the location threshold based at least in part on the system determining that the portion of the first medical device and the particular location (or portion of the image corresponding to the particular location) are not co-located when mapped to a 2D plane, do not map to the same pixel and/or do not overlap in a virtual image.

The portion of the image corresponding to the particular location can include the portions of the image received. In some embodiments, the portions of the image can include one or more pixels or an array of pixels in the image. In some embodiments, each pixel of the image corresponds to and/or can be mapped to a pixel in the imaged area. Accordingly, in some embodiments, the portion of the image that corresponds to the particular location can include the one or more pixels in the image that correspond to the one or more pixels in the imaged area that make up the particular location.

In some embodiments, the system 100 can display different locations and/or pixels with different transparency levels (e.g., different alpha transparency). Accordingly, in some embodiments, the transparency level can correspond to how transparent, opaque, and/or bright a particular location is. The system 100 can use any number of different transparency levels as desired. In certain embodiments, each transparency level is different (e.g., more/less transparent) than the other transparency levels. In some embodiments, the transparency level used can be based at least in part on a priority level of the image and/or position of the image.

At block 812, the system 100 can determine whether the portion of the first medical device satisfies a proximity threshold. In some embodiments, at block 812, the system 10 can determine the portion of the first medical device satisfies the proximity threshold. In certain embodiments, the system 10 determines the portion of the first medical device satisfies the proximity threshold before, after and/or concurrently with determining whether the portion of the first medical device satisfies the location threshold.

The proximity threshold can be based at least in part on the proximity of the portion of the first medical device with respect to the particular location and/or the point-of-view location. In some embodiments, the system 100 can determine that the portion of the first medical device satisfies the proximity threshold by determining that the portion of the first medical device is not proximal to a point-of-view location with respect to the particular location (or portion of the image corresponding to the particular location). In certain embodiments, the system 100 can determine that the portion of the first medical device satisfies the proximity threshold by determining that the portion of the first medical device is not distal to a point-of-view location with respect to the particular location (or portion of the image corresponding to the particular location).

To determine whether the portion of the first medical device is proximal to a point-of-view location with respect to the particular location, the system 100 can compare the coordinates of the portion of the first medical device to the coordinates of the particular location (or portion of the image corresponding to the particular location) and/or compare the coordinates of the portion of the virtual first medical device corresponding to the first medical device to the coordinates of the particular location mapped to the display (or portion of the image corresponding to the particular location). Similar to the coordinates compared for the location threshold described above, the coordinate that is compared can be based at least in part on the coordinate system used (e.g., display coordinate system, system coordinate system, etc.).

In some embodiments, where the x and y coordinates are used to determine whether the portion of the first medical device satisfies the location threshold, the z coordinate of the portion of the first medical device and the z coordinate of the particular location can be used to determine whether the portion of the first medical device satisfies the proximity threshold. Similarly, if the y and z coordinates are used to determine whether the portion of the first medical device satisfies the location threshold, the x coordinate can be used to determine whether the portion of the first medical device satisfies the proximity threshold. For example, when using the x coordinate to determine whether the portion of the first medical device satisfies the proximity threshold, if the x coordinate of the portion of the first medical device indicates that the portion of the first medical device is not proximal to the point-of-view location with respect to the x coordinate of the particular location, the system 100 can determine that the portion of the first medical device satisfies the proximity threshold. Similarly, if the x coordinate of the portion of the first medical device indicates that the portion of the first medical device is proximal to the point-of-view location with respect to the imaged area, the system 100 can determine that the portion of the first medical device does not satisfy the proximity threshold.

As described previously, the point-of-view location can refer to the location from which the virtual 3D space is viewed. For example, if the display is considered a window into the virtual 3D space, the point-of-view location can be the location of the window with respect to the object in the virtual 3D space. The system 100 can use the point-of-view location to draw the perspective views of the objects in the 3D space.

At block 814, based at least in part on a determination that the portion of the first medical device satisfies the proximity threshold and the location threshold, the system 100 can cause the one or more displays to display the portion of the image corresponding to the particular location at a second transparency level. As mentioned previously, the system 100 can determine that the proximity threshold is satisfied by determining that the portion of the first medical device is proximal to the point-of-view location with respect to the particular location of the imaged area. In addition, as mentioned previously, the system 100 can determine that the portion of the first medical device satisfies the location threshold in a variety of ways.

In some embodiments, the second transparency level can correspond to a transparency level that is different from the first transparency level. In certain embodiments, the second transparency level is more transparent (less opaque) than the first transparency level. In some embodiments, the second transparency level is less transparent (more opaque) than the first transparency level.

It will be understood that fewer, more, or different blocks can be used as part of the routine 800. For example, in some embodiments, the system 100 can determine that the portion of the first medical device satisfies the location threshold and the proximity threshold, and display the portion of the image corresponding to the particular location at a transparency level that is different from a transparency level when the location threshold is not satisfied.

Furthermore, the order of the blocks can be changed as desired. For example, in some embodiments, the blocks 808 and 812 can be performed in parallel. In some embodiments one or more blocks can be repeated for each location in the imaged area. For example, blocks 808-814 can be repeated for each unique location in the imaged area (or rendered image area). In addition, in any one or more of the blocks can be repeated for additional medical devices. As a non-limiting example, the system 100 can repeat blocks 802 and 808-814 for a third medical device, or additional medical devices, etc.

In some embodiments, the method can further include mapping the imaged area and/or image to a rendered image area on the one or more displays. For example, as part of processing and displaying the image, the system 100 can map the imaged area and/or image to a rendered image area on the display. As described previously, the rendered image area can be any part of the display. In some embodiments, the size of the rendered image area can correspond to the size of the imaged area. In certain embodiments, the size of the rendered image area is smaller/larger than, or equal to, the size of the imaged area. As part of the mapping, the system 100 can map each location (e.g., each pixel or group of pixels) from the imaged area to corresponding locations in the rendered image area. For example, the top, right location in the imaged area can map to the top, right location of the display image area, etc.

By mapping the imaged area to the rendered image area, the system 100 can provide the image on the display in an area that corresponds to the imaged area. Furthermore, when the system 100 determines that a particular location of the imaged area is to be displayed at a first or second transparency level, the system 100 can cause the one or more displays to display at a particular display location that corresponds to the particular location, the portion of the image at the first or second transparency level. Similarly, the system 100 can cause the one or more displays to display at the particular display location, the portion of the virtual medical device as desired.

Furthermore, in some embodiments, the system 100 can cause the one or more displays to display a portion of a virtual first medical device corresponding to the first medical device based at least in part on a determination that the portion of the first medical device satisfies the location threshold. For example, if the portion of the first medical device is level with the particular location (or otherwise satisfies the location threshold), the system 100 can cause the one or more displays to display a portion of the virtual first medical at the particular display location that corresponds to the particular location.

In addition, in certain embodiments, the system 100 can overlay the portion of the image corresponding to the particular location over (or in front of) the portion of the virtual first medical device at the second transparency level, based at least in part on the determination that the portion of the first medical device satisfies the proximity threshold. For example, if the system 100 determines that the portion of the first medical device is behind the particular location, the system 100 can display the virtual first medical device, and also display the portion of the image over the virtual first medical device. The image can be displayed more transparently than it otherwise would if the first medical device was not present at that particular location. In this way, the user can view the location of the virtual first medical device, as well as the image. Furthermore, the user can ascertain from the display that the medical device is behind the imaged area.

In certain embodiments, when the portion of the first medical device satisfies the location threshold, but does not satisfy the proximity threshold, the system 100 can cause the one or more displays to display the portion of the virtual first medical device. In such embodiments, the system 100 the system 100 can cause the one or more displays to display the portion of the virtual first medical device such that a user does not see the portion of the image corresponding to the particular location. For example, when the system 100 determines that the portion of the first medical device is co-located and/or located in front of the particular location, the system 100 can display the portion of the virtual first medical in front of, or instead of, the portion of the image.

In some embodiments, the system 100 can overlay the different display objects on the display. In some embodiments, the system 100 can cause the one or more displays to display the overlaid display objects at a rate so that a user is unable to discern any changes to the display. For example, in some embodiments, the system 100 can cause the one or more displays to display a portion of a first copy of the image corresponding to a particular location of the imaged area at the first transparency level. The system 100 can then determine whether the portion of the display object satisfies a location threshold (e.g., is level with a portion of a rendered image). For the portions of the rendered image that are level with the display object (or the display object otherwise satisfies the location threshold), the system 100 can cause the one or more displays to display a portion of a display object. The portions of the display object can be displayed over, or in front of, the portions of the first copy of the image.

In addition, the system 100 can determine whether the portion of the display object satisfies the proximity threshold. For example, the system 100 can determine whether the display object is supposed to be in front of or behind the rendered image, from the perspective of the point-of-view location. Based at least in part on a determination that the portion of the display object satisfies the location threshold and the proximity threshold, the system can cause the one or more displays to display the portion of a second copy of the image corresponding to the particular location at the second transparency level. For example, if the system 100 determines that the portion of the display object is level with and behind (or co-located with) the portion of the rendered image that corresponds to the particular location, the system 100 can cause the one or more displays to display the portion of the second copy of the image at a second transparency level (e.g., more transparent than the first transparency level), overlaid on top of (or in front of) the portion of the display object.

FIG. 8B is a flow diagram illustrative of an embodiment of a routine 850 implemented by the system 100 to display portions of a display object at different transparency levels. One skilled in the relevant art will appreciate that the elements outlined for routine 850 can be implemented by one or more computing devices/components that are associated with the system 100, such as the position sensing unit 140, the image guidance unit 130, surgical system 149, and/or imaging unit 150. Accordingly, routine 850 has been logically associated as being generally performed by the system 100. However, the following illustrative embodiment should not be construed as limiting.

At block 852, the system 100 determines a location of a first display object, as described in greater detail above with reference to block 652 of FIG. 6B. At block 854, the system 100 determines a location of a second display object, as described in greater detail above with reference to block 654 of FIG. 6B.

At block 856, the system 100 determines whether at least a portion of the first display object satisfies a location threshold. In some embodiments, at block 856, the system 100 determines that at least a portion of the first display object satisfies the location threshold. To determine whether a portion of the first display object satisfies a location threshold, the system 100 can compare the coordinates of the portion of the first display object (e.g., medical device object, image guidance cue, etc.) with the coordinates of a portion of the second display object (e.g., medical device object, image guidance cue, etc.). The portions can refer to a variety of locations within the first and/or second display objects as a whole, similar to the particular location of the imaged area, described in greater detail above. Any coordinate system can be used to compare the portions of the first and second display objects as described in greater detail above.

At block 858, based at least in part on a determination that the portion of the of the first display object does not satisfy the location threshold, the system 100 can cause the one or more displays to display the portion of the second display object at a first transparency level.

At block 860, the system 100 can determine whether the portion of the first display object satisfies a proximity threshold. In some embodiments, at block 860, the system 100 determines the portion of the first display object satisfies the proximity threshold. In certain embodiments, the system 10 determines the portion of the first display object satisfies the proximity threshold before, after and/or concurrently with determining whether the portion of the first display object satisfies the location threshold.

The proximity threshold can be based at least in part on the proximity of the portion of the first display object with respect to the portion of the second display object and the point-of-view location. In some embodiments, the system 100 can determine that the portion of the first display object satisfies the proximity threshold by determining that the portion of the first display object is not proximal to a point-of-view location with respect to the portion of the second display object. In certain embodiments, the system 100 can determine that the portion of the first display object satisfies the proximity threshold by determining that the portion of the first display object is not distal to a point-of-view location with respect to the particular location (or portion of the image corresponding to the particular location).

To determine whether the portion of the first display object is proximal to a point-of-view location with respect to the particular location, the system 100 can compare the coordinates of the portion of the first display object to the coordinates of the portion of the second medical device, as described in greater detail above.

At block 862, based at least in part on a determination that the portion of the first display object satisfies the proximity threshold and the location threshold, the system 100 can cause the one or more displays to display the portion of the second display object at a second transparency level. In some embodiments, the second transparency level can correspond to a transparency level that is different from the first transparency level. In certain embodiments, the second transparency level is more transparent (less opaque) than the first transparency level. In some embodiments, the second transparency level is less transparent more opaque) than the first transparency level.

It will be understood that fewer, more, or different blocks can be used as part of the routine 850. For example, in some embodiments, the system 100 can determine that the portion of the first display object satisfies the location threshold and the proximity threshold, and display the portion of the image corresponding to the particular location at a transparency level that is different from a transparency level when the location threshold is not satisfied.

In some embodiments, the routines 800, 850 can further include any one or any combination of the embodiments described in the '274 application and/or the embodiments described in FIGS. 4, 6A, and 6B. For example in some embodiments, the routines 800, 850 can include any one or any combination of: calculating a perspective view in a virtual 3D space of the at least one image based at least in part on the emplacement information of the second medical device with respect to the point-of-view location, causing the one or more displays to display the perspective view of the at least one image in the virtual 3D space, calculating a perspective view in the virtual 3D space of a virtual first medical device corresponding to the first medical device based at least in part on the emplacement information of the first medical device with respect to the point-of-view location and/or calculating a perspective view in the virtual 3D space of a virtual second medical device corresponding to the second medical device based at least in part on the emplacement information of the second medical device with respect to the point-of-view location, and causing the display device to display a perspective view of the at least one of the virtual first medical device and the virtual second medical device in the virtual 3D space. Any combination of the aforementioned embodiments can be used as desired.

Example Embodiments

Various example embodiments of the disclosure can be described in view of the following clauses:

Clause 1. A method, comprising:
  determining a pose of a first medical device based at least in part on received emplacement information of the first medical device;
  determining a pose of an imaged area based at least in part on received emplacement information of a second medical device;

receiving at least one image corresponding to the imaged area based at least in part on the emplacement of the second medical device;

determining whether a portion of the first medical device satisfies a location threshold;

based at least in part on a determination that the portion of the of the first medical device does not satisfy the location threshold, causing the one or more displays to display a portion of the image corresponding to a particular location of the imaged area at a first transparency level;

determining whether the portion of the first medical device satisfies a proximity threshold;

based at least in part on a determination that the portion of the first medical device satisfies the location threshold and the proximity threshold, causing the one or more displays to display the portion of the image corresponding to the particular location at a second transparency level.

Clause 2. The method of Clause 1, further comprising mapping the imaged area to a rendered image area on the one or more displays.

Clause 3. The method of Clause 1, further comprising mapping the image to a rendered image area on the one or more displays.

Clause 4. The method of Clause 3, further comprising mapping the portion of the image corresponding to the particular location to a corresponding particular display location in the rendered image area.

Clause 5. The method of Clause 4, further comprising causing the one or more displays to display at the particular display location the portion of the image at the first transparency level.

Clause 6. The method of Clause 4, further comprising causing the one or more displays to display at the particular display location the portion of the image at the second transparency level.

Clause 7. The method of Clause 1, wherein determining that the portion of the first medical device satisfies the location threshold comprises determining that the portion of the first medical device is level with the particular location of the imaged area.

Clause 8. The method of Clause 1, wherein determining that the portion of the first medical device satisfies the location threshold comprises determining that the x and y coordinates of a portion of a virtual first medical device corresponding to the portion of the first medical device match the x and y coordinates of the particular location mapped to the one or more displays.

Clause 9. The method of Clause 1, wherein determining that the portion of the first medical device satisfies the location threshold comprises determining that the y and z coordinates of the portion of the first medical device match the y and z coordinates of the particular location.

Clause 10. The method of Clause 1, wherein determining that the portion of the first medical device satisfies the location threshold comprises determining that the portion of the first medical device and the particular location are co-located on a 2D plane.

Clause 11. The method of Clause 1, wherein determining that the portion of the first medical device satisfies the location threshold comprises determining that the portion of the first medical device and the particular location are mapped to a same pixel on the one or more displays.

Clause 12. The method of Clause 1, wherein determining that the portion of the first medical device satisfies the location threshold comprises determining that the portion of the first medical device and the particular location overlap when mapped to the one or more displays.

Clause 13. The method of Clause 1, wherein determining that the portion of the first medical device satisfies the proximity threshold comprises determining that the portion of the first medical device is not proximal to a point-of-view location with respect to the particular location.

Clause 14. The method of Clause 1, wherein the point-of-view location comprises at least one of a location of a user, an expected location of user, and a fixed point relative to the one or more displays Clause 15. The method of Clause 14, wherein the point-of-view location is different for each eye of a user.

Clause 16. The method of Clause 1, wherein the first transparency level is more opaque than the second transparency level.

Clause 17. The method of Clause 1, further comprising receiving the at least one image from the second medical device.

Clause 18. The method of Clause 1, further comprising,
determining whether the portion of the first medical device satisfies the location threshold for each unique location within the imaged area;
determining whether the portion of the first medical device satisfies the proximity threshold for each unique location within the imaged area;
for each unique location in which the portion of the first medical device does not satisfy the location threshold, causing the one or more displays to display a portion of the image corresponding to the unique location of the imaged area at the first transparency level; and
for each unique location in which the portion of the first medical device satisfies the location threshold and the proximity threshold, causing the one or more displays to display the portion of the image corresponding to the unique location at the second transparency level.

Clause 19. The method of Clause 1, further comprising calculating a perspective view in a virtual 3D space of the at least one image based at least in part on the emplacement information of the second medical device with respect to the point-of-view location.

Clause 20. The method of Clause 19, further comprising causing the one or more displays to display the perspective view of the at least one image in the virtual 3D space.

Clause 21. The method of Clause 1, further comprising calculating a perspective view in the virtual 3D space of at least one of a virtual first medical device corresponding to the first medical device based at least in part on the emplacement information of the first medical device with respect to the point-of-view location and a virtual second medical device corresponding to the second medical device based at least in part on the emplacement information of the second medical device with respect to the point-of-view location.

Clause 22. The method of Clause 21, further comprising causing the display device to display a perspective view of the at least one of the virtual first medical device and the virtual second medical device in the virtual 3D space.

Clause 23. A system comprising:
 a computer system in communication with a display, the computer system comprising a computer processor and a non-transitory storage medium, wherein the computer system is configured to:
  determine a pose of a first medical device based at least in part on emplacement information of the first medical device received from a first pose sensor;
  determine a pose of an imaged area based at least in part on emplacement information of a second medical device received from a second pose sensor;
  receive at least one image corresponding to the imaged area based at least in part on the emplacement of the second medical device;
  determine whether a portion of the first medical device satisfies a location threshold;
  determine whether the portion of the first medical device satisfies a proximity threshold;
  based at least in part on a determination that the portion of the first medical device satisfies the location threshold and the proximity threshold, cause the one or more displays to display a portion of the image corresponding to a particular location in the imaged area at a first transparency level, wherein the computer system causes the one or more displays to display the portion of the image corresponding to the particular location of the imaged area at a second transparency level based at least in part on a determination that the portion of the first medical device does not satisfy the location threshold.

Clause 24. A method comprising:
 determining a location of a first display object;
 determining whether at least a portion of the first display object satisfies a location threshold;
 based at least in part on a determination that the portion of the of the first display object does not satisfy the location threshold, causing the one or more displays to display the portion of the second display object at a first transparency level;
 determining whether the portion of the first display object satisfies a proximity threshold; and
 based at least in part on a determination that the portion of the first display object satisfies the proximity threshold and the location threshold, causing the one or more displays to display the portion of the second display object at a second transparency level.

Clause 25. A computer system in communication with a display, the computer system comprising a computer processor and a non-transitory storage medium, wherein the computer system is configured to:
 determine a location of a first display object based at least in part on emplacement information of a first medical device;
 determine a location of a second display object based at least in part on emplacement information of a second medical device;
 determine whether at least a portion of the first display object is co-located with at least a portion of the second display object;
 based at least in part on a determination that the portion of the first display object is co-located with the portion of the second display object, cause the display to display one of the portion of the first display object and the portion of the second display object in front of the other of the one of the portion of the first display object and the portion of the second display object.

Clause 26. The system of Clause 25, wherein the computer system is configured to determine whether the portion of the image guidance cue from the one or more image guidance cues is co-located with the portion of a medical display object by comparing coordinates of the portion of the image guidance cue with coordinates of the portion of the medical display object.

Clause 27. The system of Clause 26, wherein the computer system is configured to adjust a coordinate of the one of the portion of the image guidance cue and the portion of the display object with respect to a point-of-view location, based at least in part on a determination that the portion of the image guidance cue is co-located with the portion of the medical display object.

Clause 28. The system of Clause 25, wherein the computer system is configured to move the one of the portion of the image guidance cue and the portion of the display object with respect to a point-of-view location.

Clause 29. The system of Clause 25, wherein the computer system is configured to move the one of the portion of the image guidance cue and the portion of the display object forward with respect to a point-of-view location.

Clause 30. The system of Clause 29, wherein the one of the portion of the image guidance cue and the portion of the display object that is moved forward is displayed at a transparency level that is greater than the transparency level of the other of the one of the portion of the image guidance cue and the portion of the display object.

Clause 31. The system of Clause 25, wherein the image guidance cue comprises at least one of an intersection indicator, a trajectory indicator and a graphic plane indicator.

Clause 32. A method, comprising:
 determining a location of a first medical device based at least in part on received emplacement information of the first medical device;
 determining a location of an imaged area based at least in part on received emplacement information of a second medical device;
 receiving at least one image corresponding to the imaged area based at least in part on the emplacement of the second medical device;
 generating one or more image guidance cues based at least in part on the determined location of the first medical device and the determined location of the imaged area;
 determining whether a portion of an image guidance cue from the one or more image guidance cues is co-located with a portion of a medical display object, wherein the medical display object comprises at least one of a first virtual medical device corresponding to the first virtual medical device corresponding to the first medical device, a second virtual medical device corresponding to the second medical device medical device, and a rendered image corresponding to the image;
 based at least in part on a determination that the portion of the image guidance cue is co-located with the portion of the medical display object, causing the one or more displays to display one of the portion of the image guidance cue and the portion of the display object in front of the other of the one of the portion of the image guidance cue and the portion of the medical display object.

Clause 33. The method of Clause 32, wherein determining whether the portion of the image guidance cue from the one or more image guidance cues is co-located with the portion of a medical display object, comprises comparing coordinates of the portion of the image guidance cue with coordinates of the portion of the medical display object.

Clause 34. The method of Clause 33, further comprising adjusting a coordinate of the one of the portion of the image guidance cue and the portion of the display object with respect to a point-of-view location, based at least in part on a determination that the portion of the image guidance cue is co-located with the portion of the medical display object.

Clause 35. The method of Clause 32, further comprising moving the one of the portion of the image guidance cue and the portion of the display object with respect to a point-of-view location.

Clause 36. The method of Clause 32, further comprising moving the one of the portion of the image guidance cue and the portion of the display object forward with respect to a point-of-view location.

Clause 37. The method of Clause 36, wherein the one of the portion of the image guidance cue and the portion of the display object that is moved forward is displayed at a transparency level that is greater than the transparency level of the other of the one of the portion of the image guidance cue and the portion of the display object.

Clause 38. The method of Clause 32, wherein the image guidance cue comprises at least one of an intersection indicator, a trajectory indicator and a graphic plane indicator.

Clause 39. A method, comprising:
 receiving a configuration command;
 determining a pose of a medical device with respect to a reference location based at least in part on received emplacement information of the medical device;
 determining a point-of-view location based at least in part on the determined pose of the medical device with respect to the reference location; and
 determining a perspective view of a virtual medical device corresponding to the medical device based at least in part on a pose of the medical device with respect to the point-of-view location, and
 causing one or more displays to display the perspective view of the virtual medical device in a virtual 3D space.

Clause 40. The method of Clause 39, further comprising determining a pose of one or more displays with respect to the reference location.

Clause 41. The method of Clause 40, further comprising determining the point-of-view location based at least in part on the determined pose of the one or more displays.

Clause 42. The method of Clause 39, wherein the reference location comprises at least one of a position sensing unit, a portion of the position sensing unit, a coordinate system of the position sensing unit, and a geographic direction.

Clause 43. The method of Clause 39, wherein the configuration command is a first configuration command, the pose of the medical device is a first pose of the medical device, the point-of-view location is a first point-of-view location, the one or more displays is a first set of one or more displays, the virtual 3D space is a first virtual 3D space, and the received emplacement information of the medical device comprises emplacement information received at a first time, the method further comprising:
 determining a second pose of the medical device with respect to the reference location based at least in part on emplacement information of the medical device received at a second time;
 determining a second point-of-view location based at least in part on the determined second pose of the medical device with respect to the reference location; and
 determining a second perspective view of the virtual medical device based at least in part on an pose of the medical device with respect to the second point-of-view location, and
 causing a second set one or more displays to display the second perspective view of the virtual medical device in a second virtual 3D space.

Clause 44. The method of Clause 39, wherein the medical device is a first medical device, the method further comprising determining a location of an imaged area based at least in part on received emplacement information of a second medical device.

Clause 45. The method of Clause 44, further comprising receiving at least one image corresponding to the imaged area based at least in part on the emplacement of the second medical device.

Clause 46. The method of Clause 45, further comprising calculating a perspective view in a virtual 3D space of the at least one image based at least in part on the emplacement information of the second medical device with respect to the point-of-view location.

Clause 47. The method of Clause 46, further comprising causing the one or more displays to display the perspective view of the at least one image in the virtual 3D space.

Clause 48. The method of Clause 44, further comprising calculating a perspective view in the virtual 3D space of a virtual second medical device corresponding to the second medical device based at least in part on the emplacement information of the second medical device with respect to the point-of-view location.

Clause 49. The method of Clause 48, further comprising causing the display device to display a perspective view of the virtual second medical device in the virtual 3D space.

Clause 50. A computer system in communication with a display, the computer system comprising a computer processor and a non-transitory storage medium, wherein the computer system is configured to: receiving a configuration command;
 determining a pose of a medical device with respect to a reference location based at least in part on received emplacement information of the medical device;
 determining a point-of-view location based at least in part on the determined pose of the medical device with respect to the reference location; and
 determining a perspective view of a virtual medical device corresponding to the medical device based at least in part on a pose of the medical device with respect to the point-of-view location, and
 causing one or more displays to display the perspective view of the virtual medical device in a virtual 3D space.

Clause 51. The system of Clause 50, wherein the computer system is further configured to determine a pose of one or more displays with respect to the reference location.

Clause 52. The system of Clause 51, wherein the computer system is further configured to determine the point-of-view location based at least in part on the determined pose of the one or more displays.

Clause 53. The system of Clause 50, wherein the reference location comprises at least one of a position sensing unit, a portion of the position sensing unit, a coordinate system of the position sensing unit, and a geographic direction.

Clause 54. The system of Clause 50, wherein the configuration command is a first configuration command, the pose of the medical device is a first pose of the medical device, the point-of-view location is a first point-of-view location, the one or more displays is a first set of one or more displays, the virtual 3D space is a first virtual 3D space, and the received emplacement information of the medical device comprises emplacement information received at a first time, and the computer system is further configured to:
- determine a second pose of the medical device with respect to the reference location based at least in part on emplacement information of the medical device received at a second time;
- determine a second point-of-view location based at least in part on the determined second pose of the medical device with respect to the reference location; and
- determine a second perspective view of the virtual medical device based at least in part on an pose of the medical device with respect to the second point-of-view location, and
- cause a second set one or more displays to display the second perspective view of the virtual medical device in a second virtual 3D space.

Clause 55. The system of Clause 50, wherein the medical device is a first medical device, and wherein the computer system is further configured to determine a location of an imaged area based at least in part on received emplacement information of a second medical device.

Clause 56. The system of Clause 55, wherein the computer system is further configured to receive at least one image corresponding to the imaged area based at least in part on the emplacement of the second medical device.

Clause 57. The system of Clause 56, wherein the computer system is further configured to calculate a perspective view in a virtual 3D space of the at least one image based at least in part on the emplacement information of the second medical device with respect to the point-of-view location.

Clause 58. The system of Clause 57, wherein the computer system is further configured to cause the one or more displays to display the perspective view of the at least one image in the virtual 3D space.

Clause 59. The system of Clause 55, wherein the computer system is further configured to calculate a perspective view in the virtual 3D space of a virtual second medical device corresponding to the second medical device based at least in part on the emplacement information of the second medical device with respect to the point-of-view location.

Clause 60. The system of Clause 59, wherein the computer system is further configured to cause the display device to display a perspective view of the virtual second medical device in the virtual 3D space.

Terminology

Those having skill in the art will further appreciate that the various illustrative logical blocks, modules, circuits, and process steps described in connection with the implementations disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present invention. One skilled in the art will recognize that a portion, or a part, can comprise something less than, or equal to, a whole. For example, a portion of a collection of pixels can refer to a sub-collection of those pixels.

The various illustrative logical blocks, modules, and circuits described in connection with the implementations disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The steps of a method or process described in connection with the implementations disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory storage medium known in the art. An exemplary computer-readable storage medium is coupled to the processor such the processor can read information from, and write information to, the computer-readable storage medium. In the alternative, the storage medium can be integral to the processor. The processor and the storage medium can reside in an ASIC. The ASIC can reside in a user terminal, camera, or other device. In the alternative, the processor and the storage medium can reside as discrete components in a user terminal, camera, or other device.

Headings are included herein for reference and to aid in locating various sections. These headings are not intended to limit the scope of the concepts described with respect thereto. Such concepts can have applicability throughout the entire specification.

The previous description of the disclosed implementations is provided to enable any person skilled in the art to make or use the present invention. Various modifications to these implementations will be readily apparent to those skilled in the art, and the generic principles defined herein can be applied to other implementations without departing from the spirit or scope of the invention. Furthermore, although described above with reference to medical devices and procedures, it will be understood that the embodiments described herein can be applied to other systems in which objects are tracked and virtual representations are displayed on a display and/or systems in which multiple objects are displayed on a display within a virtual space, such as within a virtual 3D space. Thus, the present invention is not intended to be limited to the implementations shown herein but is to be accorded the widest scope consistent with the principles and novel features disclosed herein.

The invention claimed is:

1. A method for displaying portions of at least one medical image at different transparency levels based on a relative location and proximity to a determined virtual medical device, the method comprising:
   receiving, from a tracking system, first emplacement information with an emplacement of a first medical device;
   determining, with one or more processors, a pose of a first virtual medical device based at least in part on the received first emplacement information;
   receiving, from the tracking system, second emplacement information associated with an emplacement of a second medical device;
   receiving, from the second medical device, at least one medical image corresponding to an imaged area, wherein the imaged area corresponds to an area that is captured by the second medical device when the second medical device acquires the at least one medical image;
   determining, with the one or more processors, a pose of the imaged area based at least in part on the received second emplacement information;
   determining whether a portion of the first virtual medical device satisfies a location threshold with respect to a particular location of the imaged area based at least in part on the determined pose of the first virtual medical device and the determined pose of the imaged area;
   based at least in part on a determination that the portion of the first virtual medical device does not satisfy the location threshold, causing one or more displays to display a portion of the at least one medical image corresponding to the particular location of the imaged area at a first transparency level;
   determining whether the portion of the first virtual medical device satisfies a proximity threshold with respect to the particular location of the imaged area based at least in part on the determined pose of the first virtual medical device and the determined pose of the imaged area; and
   based at least in part on a determination that the portion of the first virtual medical device satisfies the location threshold and the proximity threshold, causing the one or more displays to display the portion of the at least one medical image corresponding to the particular location at a second transparency level.

2. The method of claim 1, further comprising mapping the imaged area to a rendered image area on the one or more displays.

3. The method of claim 1, further comprising mapping the at least one medical image to a rendered image area on the one or more displays.

4. The method of claim 3, further comprising mapping the portion of the at least one medical image corresponding to the particular location to a corresponding particular display location in the rendered image area.

5. The method of claim 4, further comprising causing the one or more displays to display at the particular display location the portion of the at least one medical image at the first transparency level.

6. The method of claim 4, further comprising causing the one or more displays to display at the particular display location the portion of the at least one medical image at the second transparency level.

7. The method of claim 1, wherein the determination that the portion of the first virtual medical device satisfies the location threshold comprises determining that the portion of the first virtual medical device is level with the particular location of the imaged area.

8. The method of claim 1, wherein the determination that the portion of the first virtual medical device satisfies the location threshold comprises determining that x- and y-coordinates of the portion of the first virtual medical device match x- and y-coordinates of the particular location mapped to the one or more displays.

9. The method of claim 1, wherein the determination that the portion of the first virtual medical device satisfies the location threshold comprises determining that y- and z-coordinates of the portion of the first virtual medical device match y- and z-coordinates of the particular location.

10. The method of claim 1, wherein the determination that the portion of the first virtual medical device satisfies the location threshold comprises determining that the portion of the first virtual medical device and the particular location are co-located on a 2D plane defined by the one or more displays.

11. The method of claim 1, wherein the determination that the portion of the first virtual medical device satisfies the location threshold comprises determining that the portion of the first virtual medical device is mapped to a pixel, on the one or more displays, that the particular location is mapped to.

12. The method of claim 1, wherein the determination that the portion of the first virtual medical device satisfies the location threshold comprises determining that the portion of the first virtual medical device and the particular location overlap when mapped to the one or more displays.

13. The method of claim 1, wherein the determination that the portion of the first virtual medical device satisfies the proximity threshold comprises determining that the portion of the first virtual medical device is not proximal to a point-of-view location with respect to the particular location.

14. The method of claim 13, wherein the point-of-view location comprises at least one of a location of a user, an expected location of the user, or a fixed point relative to the one or more displays.

15. The method of claim 14, wherein the point-of-view location is different for each eye of the user.

16. The method of claim 1, wherein the first transparency level is more opaque than the second transparency level.

17. The method of claim 1, further comprising receiving the at least one medical image from the second medical device.

18. The method of claim 1, further comprising,
   determining, with the one or more processors, whether the portion of the first virtual medical device satisfies the location threshold for each unique location within the imaged area;
   determining, with the one or more processors, whether the portion of the first virtual medical device satisfies the proximity threshold for each unique location within the imaged area;

for each unique location in which the portion of the first virtual medical device does not satisfy the location threshold, causing the one or more displays to display a portion of the at least one medical image corresponding to the unique location of the imaged area at the first transparency level; and for each unique location in which the portion of the first virtual medical device satisfies the location threshold and the proximity threshold, causing the one or more displays to display the portion of the at least one medical image corresponding to the unique location at the second transparency level.

19. The method of claim 1, further comprising calculating a perspective view in a virtual 3D space of the at least one medical image based at least in part on the second emplacement information associated with the emplacement of the second medical device with respect to a point-of-view location.

20. The method of claim 19, further comprising causing the one or more displays to display the perspective view of the at least one medical image in the virtual 3D space.

21. The method of claim 19, further comprising calculating a perspective view in the virtual 3D space of at least one of the first virtual medical device corresponding to the first medical device based at least in part on the received first emplacement information respect to the point-of-view location or a second virtual medical device corresponding to the second medical device based at least in part on the received second emplacement information with respect to the point-of-view location.

22. The method of claim 21, further comprising causing the one or more displays to display a perspective view of the at least one of the first virtual medical device or the second virtual medical device in the virtual 3D space.

23. A system for displaying portions of a medical image at different transparency levels based on a relative location and proximity to a determined virtual medical device, the system comprising:

a computer system in communication with one or more displays, the computer system comprising a computer processor and a non-transitory storage medium, wherein the computer system is configured to:

receive, from a tracking system, first emplacement information associated with an emplacement of a first medical device;

determine a pose of a first virtual medical device based at least in part on the received first emplacement information;

receive, from a second medical device, at least one medical image corresponding to an imaged area, wherein the imaged area corresponds to an area that is captured by the second medical device when the second medical device acquires the at least one medical image;

determine a pose of the imaged area based at least in part on second emplacement information associated with an emplacement of the second medical device, the second emplacement information received from the tracking system;

determine whether a portion of the first virtual medical device satisfies a location threshold based at least in part on the determined pose of the first virtual medical device and the determined pose of the imaged area;

determine whether the portion of the first virtual medical device satisfies a proximity threshold based at least in part on the determined pose of the first virtual medical device and the determined pose of the imaged area; and based at least in part on a determination that the portion of the first virtual medical device satisfies the location threshold and the proximity threshold, cause the one or more displays to display a portion of the at least one medical image corresponding to a particular location of the imaged area at a first transparency level, wherein the computer system causes the one or more displays to display the portion of the at least one medical image corresponding to the particular location of the imaged area at a second transparency level based at least in part on a determination that the portion of the first virtual medical device does not satisfy the location threshold.

24. A method for displaying portions of a display object at different transparency levels based on a relative location and proximity to another display object, the method comprising:

receiving, with one or more processors, first emplacement information from a tracking system, the first emplacement information associated with an emplacement of a first object;

determining, with the one or more processors, a location of a first display object based at least in part on the first emplacement information;

determining, with the one or more processors, a location of a second display object based at least in part on second emplacement information received from the tracking system;

determining, with the one or more processors, whether at least a portion of the first display object satisfies a location threshold with respect to the second display object based at least in part on the determined location of the first display object and the determined location of the second display object;

based at least in part on a determination that the portion of the first display object does not satisfy the location threshold, causing one or more displays to display the portion of the second display object at a first transparency level;

determining, with the one or more processors, whether the portion of the first display object satisfies a proximity threshold with respect to the second display object based at least in part on the determined location of the first display object and the determined location of the second display object; and based at least in part on a determination that the portion of the first display object satisfies the proximity threshold and the location threshold, causing the one or more displays to display the portion of the second display object at a second transparency level.

* * * * *